(12) United States Patent
Pinheiro et al.

(10) Patent No.: US 9,309,300 B2
(45) Date of Patent: Apr. 12, 2016

(54) CHROMOSOMAL INSERTION OF GFP INTO BACTERIA FOR QUALITY CONTROL

(75) Inventors: Leonardo B. Pinheiro, Avalon (AU);
Peter Bergquist, Auckland (NZ);
Moreland Gibbs, Turramurra (AU);
Graham Vesey, Hornsby (AU)

(73) Assignees: MACQUARIE UNIVERSITY, New South Wales (AU); BTF PTY LTD., New South Wales (AU)

( * ) Notice: Subject to any disclaimer, the term of this patent is extended or adjusted under 35 U.S.C. 154(b) by 0 days.

(21) Appl. No.: 13/566,227

(22) Filed: Aug. 3, 2012

(65) Prior Publication Data

US 2013/0065297 A1  Mar. 14, 2013

Related U.S. Application Data

(63) Continuation of application No. 11/662,801, filed as application No. PCT/AU2005/001387 on Sep. 12, 2005, now abandoned.

(30) Foreign Application Priority Data

Sep. 14, 2004 (AU) ................................ 2004905286

(51) Int. Cl.
*C07K 14/435* (2006.01)

(52) U.S. Cl.
CPC ................................ *C07K 14/43595* (2013.01)

(58) Field of Classification Search
None
See application file for complete search history.

(56) References Cited

U.S. PATENT DOCUMENTS 6,090,919 A  7/2000  Cormack et al.

FOREIGN PATENT DOCUMENTS

| NL | 1012782 C2 | 2/2001 |
|---|---|---|
| WO | WO/96/23810 | 8/1996 |
| WO | WO 00/08054 | 2/2000 |
| WO | WO 2006/029449 | 3/2006 |

OTHER PUBLICATIONS

Jordan, Edwin., Botanical Gazette (1899), vol. 27, pp. 19-24.*
Suarez, et al., "Green fluorescent protein-based reporter systems for genetic analysis of bacteria including monocopy applications," *Gene* 196: 69-74, Elsevier Science B.V., Braunschweig, Germany (1997).
Stretton, et al., "Use of Green Fluorescent Protein to Tag and Investigate Gene Expression in Marine Bacteria," *Appl. Environ. Microbiol.* 64(7): 2554-2559, American Society for Microbiology, United States (1998).
International Search Report mailed Oct. 17, 2005 in the International (PCT) Application No. PCT/AU2005/001387 which the present application is the U.S. National Stage.
Sheff et al., "Optimized casettes for fluorescent protein tagging in *Saccharomyces cerevisiae*," *Yeast* Jun. 2004, vol. 21, pp. 661-670 (2004).

(Continued)

*Primary Examiner* — Alexander Kim
(74) *Attorney, Agent, or Firm* — Cooley LLP

(57) ABSTRACT

An isolated mutated green fluorescent protein (gfp) gene for chromosomal insertion into a bacterium, wherein the gene is capable of being expressed in bacteria and produce sufficient fluorescence under illumination from a UV lamp in a bacterial colony to be seen by the naked eye. A gene cassette for inserting a gene into a chromosome.

13 Claims, 12 Drawing Sheets

(56) References Cited

OTHER PUBLICATIONS

Nomura et al. Functional expression of green fluorescent protein derivatives in *Halobacterium salinarum.*, *FEMS Microbiology Letters*, 1998, vol. 167, pp. 287-293.

Pinheiro et al., Fluorescent reference strains of bacteria by chromosomal integration of a modified green fluorescent protein gene., *Appl. Microbial. Biotechnol.*, E pub Nov. 9, 2007, vol. 77, pp. 1287-1295.

Tsien, The Green Fluorescent Protein, *Annu. Rev. Biochem.*, 1998, vol. 67, pp. 509-544.

Poronnik et al. Use of replication deficient adenoviruses to investigate the role of G proteins in Ca2+ signalling in epithelial cells., *Cell Calcium*, 1998, vol. 24, pp. 97-103.

Lohman et al., Large-scale overproduction and rapid purification of the *Escherichia coli* ssb gene product. Expression of the ssb gene under lambda PL control, *Biochemistry*, 1986, vol. 25 (1), pp. 21-25.

Sadava et al. Life, the science of biology, (2006) Sinauer Associates Inc., Eighth Edition, p. 293.

Hautefort et al., Single-Copy Green Fluorescent Protein Gene Fusions Allow Accurate Measurement of *Salmonella* Gene Expression in Vitro and during Infection of Mammalian Cells, *Appl. Environ. Microbial.* (Dec. 2003), vol. 69, pp. 7480-7491.

Lee et al., Sequential a-Integration for the Regulated Insertion of Cloned Genes in *Saccharomyces cerevisiae.*, *Biotechnol., Prog.* (1997), vol. 13, pp. 368-373.

Freitag et al., Examination of *Listeria monocytogenes* Intracellular Gene Expression by Using the Green Fluorescent Protein of *Aequorea victoria, Infect Immun.* (Apr. 1999), vol. 67, No. 4, pp. 1844-1852.

* cited by examiner

```
                 SalI
  1 AAAAAAAAAAGTCGACTCAGCCAAACGTCTCTTCAGGCCACTGACTAGCGATAACTTTCC  60
                     *  G  F  T  E  E  P  W  Q  S  A  I  V  K

61 CCACAACGGAACAACTCTCATTGCATGGATCATTGGGTACTGTGGGTTTAGTGGTTGTA 120
     G  V  V  S  C  S  E  N  C  P  I  M  P  Y  Q  P  N  L  P  Q

121 AAAACACCTGACCGCTATCCCTGATCAGTTTCTTGAAGGTAAACTCATCACCCCCAAGTC 180
     L  F  V  Q  G  S  D  R  I  L  K  K  F  T  F  E  D  G  G  L

181 TGGCTATGCAGAAATCACCTGGCTCAACAGCCTGCTCAGGGTCAACGAGAATTAACATTC 240
     R  A  I  C  F  D  G  P  E  V  A  Q  E  P  D  V  L  I  L  M

241 CGTCAGGAAAGCTTGGCTTGGAGCCTGTTGGTGCGGTCATGGAATTACCTTCAACCTCAA 300
     G  D  P  F  S  P  K  S  G  T  P  A  T  M  S  N  G  E  V  E

301 GCCAGAATGCAGAATCACTGGCTTTTTTGGTTGTGCTTACCCATCTCTCCGCATCACCTT 360
     L  W  F  A  S  D  S  A  K  K  T  T  S  V  W  R  E  A  D  G

361 TGGTAAAGGTTCTAAGCTTAGGTGAGAACATCCCTGCCTGAACATGAGAAAAAACAGGGT 420
     K  T  F  T  R  L  K  P  S  F  M  G  A  Q  V  H  S  F  V  P

421 ACTCATACTCACTTCTAAGTGACGGCTGCATACTAACCGCTTCATACATCTCGTAGATTT 480
     Y  E  Y  E  S  R  L  S  P  Q  M  S  V  A  E  Y  M  E  Y  I

481 CTCTGGCGATTGAAGGGCTAAATTCTTCAACGCTAACTTTGAGAATTTTTGTAAGCAATG 540
     E  R  A  I  S  P  S  F  E  E  V  S  V  K  L  I  K  T  L  L

541 CGGCGTTATAAGCATTTAATGCATTGATGCCATTAAATAAAGCACCAACGCCTGACTGCC 600
     A  A  N  Y  A  N  L  A  N  I  G  N  F  L  A  G  V  S  Q
```

Figure 3 continued

```
601 CCATCCCCATCTTGTCTGCGACAGATTCCTGGGATAAGCCAAGTTCATTTTTCTTTTTTT 660
     G   M   G   M   K   D   A   V   S   E   Q   S   L   G   L   E   N   K   K   K

661 CATAAATTGCTTTAAGGCGACGTGCGTCCTCAAGCTGCTCTTGTGTTAATGGTTTCTTTT 720
     E   Y   I   A   K   L   R   R   A   D   E   L   Q   E   Q   T   L   P   K   K

R3                             R2
721 TTGTGCTCATACGTTAAATCTATCACCGCAAGGGATAAATATCTAACACCGTGCGTGTTG 780
     K   T   S   M      (SEQ ID NO 2)
                  R1
781 ACTATTTTACCTCTGGCGGTGATAATGGTTGCATGTACTAAGGAGGTTGTATGGAACAAC 840

841 GCATAACCCTGAAAGATTATGCAATGCGCTTTGGGCAAACCAAGACAGCTAAAGATCAAG 900

901 AATGTTGATCTTCAGTGTTTCGCCTGTCTGTTTTGCACCGGAATTTTTGAGTTCTGCCGT 960

SmaI
961 TTATCGCCCGGGGATCTCTCACCTACCAAACAATGCCCCCCTGCAAAAAATAAATTCATA 1020

L3                  L2
1021 TAAAAAACATACAGATAACCATCTGCGGTGATAAATTATCTCTGGCGGTGTTGACATAAA 1080

L1
1081 TACCACTGGCGGTGATACTGAGCACATCAGCAGGACGCACTGACCACCATGAAGGTGACG 1140

1141 CTCTTAAAAATTAAGCCCTGAAGAAGGGCAGCATTCAAAGCAGAAGGCTTTGGGGTGTGT 1200

XhoI
1201 GATACGAAACGAAGCATTGGCGCCTCGAGTAATTTACCAACACTACTACGTTTTAACTGA 1260
```

Figure 3 continued

```
1261 AACAAACTGGAGACTGCCATGAGTAAAGGAGAAGAACTTTTCACTGGAGTTGTCCCAATT 1320
                    M  S  K  G  E  E  L  F  T  G  V  V  P  I

1321 CTTGTTGAATTAGATGGTGATGTTAATGGGCACAAATTTTCTGTCAGTGGAGAGGGTGAA 1380
      L  V  E  L  D  G  D  V  N  G  H  K  F  S  V  S  G  E  G  E

1381 GGTGATGCAACATACGGAAAACTTACCCTTAAATTTATTTGCACTACTGGAAAACTACCT 1440
      G  D  A  T  Y  G  K  L  T  L  K  F  I  C  T  T  G  K  L  P

1441 GTTCCATGGCCAACACTTGTCACTACTTTCKSKTATGGTSTTCAATGCTTTKCRAGATAC 1500
      V  P  W  P  T  L  V  T  T  F  S  Y  G  V  Q  C  F  S  R  Y
                                    A     L           A
                                    G

1501 CCAGATCATATGAAACGGCATGACTTTTTCAAGAGTGCCATGCCCGAAGGTTATGTACAG 1560
      P  D  H  M  K  R  H  D  F  F  K  S  A  M  P  E  G  Y  V  Q

1561 GAAAGAACTATATYTTTCAAAGATGACGGGAACTACAAGACACGTGCTGAAGTCAAGTTT 1620
      E  R  T  I  F  F  K  D  D  G  N  Y  K  T  R  A  E  V  K  F
                S

1621 GAAGGTGATACCCTTGTTAATAGAATCGAGTTAAAAGGTATTGATTTTAAAGAAGATGGA 1680
      E  G  D  T  L  V  N  R  I  E  L  K  G  I  D  F  K  E  D  G

1681 AACATTCTTGGACACAAATTGGAATACAACTATAACTCACACAATGTATACATCATYGCA 1740
      N  I  L  G  H  K  L  E  Y  N  Y  N  S  H  N  V  Y  I  M  A
                                                              T

1741 GACAAACAAAAGAATGGAATCAAAGYTAACTTCAAAATTAGACACAACATTGAAGATGGA 1800
      D  K  Q  K  N  G  I  K  V  N  F  K  I  R  H  N  I  E  D  G
                          A
```

Figure 3 continued

```
1801 AGCGTTCAACTAGCAGACCATTATCAACAAAATACTCCAATTGGCGATGGCCCTGTCCTT 1860
      S   V   Q   L   A   D   H   Y   Q   Q   N   T   P   I   G   D   G   P   V   L

1861 TTACCAGACAACCATTACCTGTCCACACAATCTGCCCTTTCGAAAGATCCCAACGAAAAG 1920
      L   P   D   N   H   Y   L   S   T   Q   S   A   L   S   K   D   P   N   E   K

1921 AGAGACCACATGGTCCTTCTTGAGTTTGTAACAGCTGCTGGGATTACACATGGCATGGAT 1980
      R   D   H   M   V   L   L   E   F   V   T   A   A   G   I   T   H   G   M   D

EcoRI
1981 GAACTATACAAATAAGAATTCAAAAAA 2007 (SEQ ID NO 1)
      E   L   Y   K   *           (SEQ ID NO 3)-
```

Figure 4

```
     BglII
  1  AGATCTGAAGCGGCGCACGAAAAACGCGAAAGCGTTTCACGATAAATGCGAAAACGGATC   60

61  CTTTTCGACCGAATAAATACCTGTGACGGAAGATCACTTCGCAGAATAAATAAATCCTGG  120

121  TGTCCCTGTTGATACCGGGAAGCCCTGGGCCAACTTTTGGCGAAAATGAGACGTTGATCG  180

181  GCACGTAAGAGGTTCCAACTTTCACCATAATGAAATAAGATCACTACCGGGCGTATTTTT  240

241  TGAGTTGTCGAGATTTTCAGGAGCTAAGGAAGCTAAAATGGAGAAAAAAATCACTGGATA  300
                                            M  E  K  K  I  T  G  Y

301  TACCACCGTTGATATATCCCAATGGCATCGTAAAGAACATTTTGAGGCATTTCAGTCAGT  360
      T  T  V  D  I  S  Q  W  H  R  K  E  H  F  E  A  F  Q  S  V

361  TGCTCAATGTACCTATAACCAGACCGTTCAGCTGGATATTACGGCCTTTTTAAAGACCGT  420
      A  Q  C  T  Y  N  Q  T  V  Q  L  D  I  T  A  F  L  K  T  V

421  AAAGAAAAATAAGCACAAGTTTTATCCGGCCTTTATTCACATTCTTGCCCGCCTGATGAA  480
      K  K  N  K  H  K  F  Y  P  A  F  I  H  I  L  A  R  L  M  N

481  TGCTCATCCGGAATTACGTATGGCAATGAAAGACGGTGAGCTGGTGATATGGGATAGTGT  540
      A  H  P  E  L  R  M  A  M  K  D  G  E  L  V  I  W  D  S  V

541  TCACCCTTGTTACACCGTTTTCCATGAGCAAACTGAAACGTTTTCATCGCTCTGGAGTGA  600
      H  P  C  Y  T  V  F  H  E  Q  T  E  T  F  S  S  L  W  S  E

601  ATACCACGACGATTTCCGGCAGTTTCTACACATATATTCGCAAGATGTGGCGTGTTACGG  660
      Y  H  D  D  F  R  Q  F  L  H  I  Y  S  Q  D  V  A  C  Y  G
```

Figure 4 continued

```
 661  TGAAAACCTGGCCTATTTCCCTAAAGGGTTTATTGAGAATATGTTTTTCGTCTCAGCCAA   720
        E  N  L  A  Y  F  P  K  G  F  I  E  N  M  F  F  V  S  A  N

721  TCCCTGGGTGAGTTTCACCAGTTTTGATTTAAACGTGGCCAATATGGACAACTTCTTCGC   780
        P  W  V  S  F  T  S  F  D  L  N  V  A  N  M  D  N  F  F  A

781  CCCCGTTTTCACCATGGGCAAATATTATACGCAAGGCGACAAGGTGCTGATGCCGCTGGC   840
        P  V  F  T  M  G  K  Y  Y  T  Q  G  D  K  V  L  M  P  L  A

841  GATTCAGGTTCATCATGCCGTTTGTGATGGCTTCCATGTCGGCAGAATGCTTAATGAATT   900
        I  Q  V  H  H  A  V  C  D  G  F  H  V  G  R  M  L  N  E  L

901  ACAACAGTACTGCGATGAGTGGCAGGGCGGGGCGTAATTTTTTAAGGCAGTTATTGGTG    960
        Q  Q  Y  C  D  E  W  Q  G  G  A  *  (SEQ ID NO 5)

961  CCCTTAAACGCCTGGTTGCTACGCCTGAATAAGTGATAATAAGCGGATGAATGGCAGAAA  1020

1021  TTCGAAAGCAAATTCGACCCGGTCGTCGGTTCAGGGCAGGGTCGTTAAATAGCCGCTTAT  1080

1081  GTCTATTGCTGGTTTACCGGTTTATTGACTACCGGAAGCAGTGTGACCGTGTGCTTCTCA  1140

1141  AATGCCTGAGGCCAGTTTGCTCAGGCTCTCCCCGTGGAGGTAATAATTGACGATAGGATC  1200
                 EcoRV/SmaI blunt-end ligation point
1201  CGCGGCCGGCCGATGGGGATCTCTCACCTACCAAACAATGCCCCCCTGCAAAAAATAAAT  1260
                                    L3                     L2
1261  TCATATAAAAAACATACAGATAACCATCTGCGGTGATAAATTATCTCTGGCGGTGTTGAC  1320
```

Figure 4 continued

```
                  L1
1321  ATAAATACCACTGGCGGTGATACTGAGCACATCAGCAGGACGCACTGACCACCATGAAGG  1380

1381  TGACGCTCTTAAAAATTAAGCCCTGAAGAAGGGCAGCATTCAAAGCAGAAGGCTTTGGGG  1440

XhoI
1441  TGTGTGATACGAAACGAAGCATTGGCGCCTCGAGTAATTTACCAACACTACTACGTTTTA  1500

1501  ACTGAAACAAACTGGAGACTGCCATGAGTAAAGGAGAAGAACTTTTCACTGGAGTTGTCC  1560
                        M  S  K  G  E  E  L  F  T  G  V  V  P

1561  CAATTCTTGTTGAATTAGATGGTGATGTTAATGGGCACAAATTTTCTGTCAGTGGAGAGG  1620
       I  L  V  E  L  D  G  D  V  N  G  H  K  F  S  V  S  G  E  G

1621  GTGAAGGTGATGCAACATACGGAAAACTTACCCTTAAATTTATTTGCACTACTGGAAAAC  1680
       E  G  D  A  T  Y  G  K  L  T  L  K  F  I  C  T  T  G  K  L

S72A
1681  TACCTGTTCCATGGCCAACACTTGTCACTACTTTCTCTTATGGTGTTCAATGCTTTGCGA  1740
       P  V  P  W  P  T  L  V  T  T  F  S  Y  G  V  Q  C  F  A  R

1741  GATACCCAGATCATATGAAACGGCATGACTTTTTCAAGAGTGCCATGCCCGAAGGTTATG  1800
       Y  P  D  H  M  K  R  H  D  F  F  K  S  A  M  P  E  G  Y  V

1801  TACAGGAAAGAACTATATTTTTCAAAGATGACGGGAACTACAAGACACGTGCTGAAGTCA  1860
       Q  E  R  T  I  F  F  K  D  D  G  N  Y  K  T  R  A  E  V  K

1861  AGTTTGAAGGTGATACCCTTGTTAATAGAATCGAGTTAAAAGGTATTGATTTTAAAGAAG  1920
       F  E  G  D  T  L  V  N  R  I  E  L  K  G  I  D  F  K  E  D
```

Figure 4 continued

```
                                                                  M153T
1921  ATGGAAACATTCTTGGACACAAATTGGAATACAACTATAACTCACACAATGTATACATCA  1980
        G  N  I  L  G  H  K  L  E  Y  N  Y  N  S  H  N  V  Y  I  T

V163A
1981  CGGCAGACAAACAAAAGAATGGAATCAAAGCTAACTTCAAAATTAGACACAACATTGAAG  2040
        A  D  K  Q  K  N  G  I  K  A  N  F  K  I  R  H  N  I  E  D

2041  ATGGAAGCGTTCAACTAGCAGACCATTATCAACAAAATACTCCAATTGGCGATGGCCCTG  2100
        G  S  V  Q  L  A  D  H  Y  Q  Q  N  T  P  I  G  D  G  P  V

2101  TCCTTTTACCAGACAACCATTACCTGTCCACACAATCTGCCCTTTCGAAAGATCCCAACG  2160
        L  L  P  D  N  H  Y  L  S  T  Q  S  A  L  S  K  D  P  N  E

2161  AAAAGAGAGACCACATGGTCCTTCTTGAGTTTGTAACAGCTGCTGGGATTACACATGGCA  2220
        K  R  D  H  M  V  L  L  E  F  V  T  A  A  G  I  T  H  G  M

EcoRI
2221  TGGATGAACTATACAAATAAGAATTCTCTAGATGATCAGCGGCCGCGATCCGTTTTCGCA  2280
        D  E  L  Y  K  *   (SEQ ID NO 6)
                                                     BglII
2281  TTTATCGTGAAACGCTTTCGCGTTTTTCGTGCGCCGCTTCAGATCT  2326 (SEQ ID NO 4)
```

Figure 5

```
  1 GGGGATCTCTCACCTACCAAACAATGCCCCCCTGCAAAAAATAAATTCATATAAAAAACA  60

L3                    L2                       L1
 61 TACAGATAACCATCTGCGGTGATAAATTATCTCTGGCGGTGTTGACATAAATACCACTGG 120

121 CGGTGATACTGAGCACATCAGCAGGACGCACTGACCACCATGAAGGTGACGCTCTTAAAA 180

181 ATTAAGCCCTGAAGAAGGGCAGCATTCAAAGCAGAAGGCTTTGGGGTGTGTGATACGAAA 240

XhoI
241 CGAAGCATTGGCGCCTCGAGTAATTTACCAACACTACTACGTTTTAACTGAAACAAACTG 300

301 GAGACTGCCATGAGTAAAGGAGAAGAACTTTTCACTGGAGTTGTCCCAATTCTTGTTGAA 360
              M  S  K  G  E  E  L  F  T  G  V  V  P  I  L  V  E

361 TTAGATGGTGATGTTAATGGGCACAAATTTTCTGTCAGTGGAGAGGGTGAAGGTGATGCA 420
     L  D  G  D  V  N  G  H  K  F  S  V  S  G  E  G  E  G  D  A

421 ACATACGGAAAACTTACCCTTAAATTTATTTGCACTACTGGAAAACTACCTGTTCCATGG 480
     T  Y  G  K  L  T  L  K  F  I  C  T  T  G  K  L  P  V  P  W

S72A
481 CCAACACTTGTCACTACTTTCTCTTATGGTGTTCAATGCTTTGCGAGATACCCAGATCAT 540
     P  T  L  V  T  T  F  S  Y  G  V  Q  C  F  A  R  Y  P  D  H
```

Figure 5 continued

```
541  ATGAAACGGCATGACTTTTTCAAGAGTGCCATGCCCGAAGGTTATGTACAGGAAAGAACT  600
      M   K   R   H   D   F   F   K   S   A   M   P   E   G   Y   V   Q   E   R   T

601  ATATTTTTCAAAGATGACGGGAACTACAAGACACGTGCTGAAGTCAAGTTTGAAGGTGAT  660
      I   F   F   K   D   D   G   N   Y   K   T   R   A   E   V   K   F   E   G   D

661  ACCCTTGTTAATAGAATCGAGTTAAAAGGTATTGATTTTAAAGAAGATGGAAACATTCTT  720
      T   L   V   N   R   I   E   L   K   G   I   D   F   K   E   D   G   N   I   L

M153T
721  GGACACAAATTGGAATACAACTATAACTCACACAATGTATACATCACGGCAGACAAACAA  780
      G   H   K   L   E   Y   N   Y   N   S   H   N   V   Y   I   T   A   D   K   Q

V163A
781  AAGAATGGAATCAAAGCTAACTTCAAAATTAGACACAACATTGAAGATGGAAGCGTTCAA  840
      K   N   G   I   K   A   N   F   K   I   R   H   N   I   E   D   G   S   V   Q

841  CTAGCAGACCATTATCAACAAAATACTCCAATTGGCGATGGCCCTGTCCTTTTACCAGAC  900
      L   A   D   H   Y   Q   Q   N   T   P   I   G   D   G   P   V   L   L   P   D

901  AACCATTACCTGTCCACACAATCTGCCCTTTCGAAAGATCCCAACGAAAAGAGAGACCAC  960
      N   H   Y   L   S   T   Q   S   A   L   S   K   D   P   N   E   K   R   D   H

961  ATGGTCCTTCTTGAGTTTGTAACAGCTGCTGGGATTACACATGGCATGGATGAACTATAC  1020
      M   V   L   L   E   F   V   T   A   A   G   I   T   H   G   M   D   E   L   Y

EcoRI
1021 AAATAAGAATTC  1032 (SEQ ID NO 7)
      K   *       (SEQ ID NO 8)
```

CHROMOSOMAL INSERTION OF GFP INTO BACTERIA FOR QUALITY CONTROL

CROSS REFERENCE TO RELATED APPLICATIONS

This application is a continuation of U.S. patent application Ser. No. 11/662,801, which is a national stage application of PCT/AU2005/001387 filed Sep. 12, 2005, which claims priority to Australian Patent Application No. 2004905286, filed Sep. 14, 2004, which are incorporated by reference herein in their entireties.

TECHNICAL FIELD

The present invention is directed to methods for producing labelled cells, particularly visibly fluorescent bacteria suitable for use as quality control strains in microbiological or biological testing.

DESCRIPTION OF THE TEXT FILE SUBMITTED ELECTRONICALLY

The contents of the text file submitted electronically herewith are incorporated herein by reference in their entirety: A computer readable format copy of the Sequence Listing of the Sequence Listing (filename: ALLE_016_01US_SubSeqList_ST25.txt, date recorded: Nov. 12, 2012, file size 22 kilobytes).

BACKGROUND

Microbiology testing laboratories maintain in-house culture collections of microorganisms for quality control purposes. These microorganisms are known as quality control (QC) strains and are used as reference standards and for quality control of the testing methods. Samples that are known to be free of contamination are often spiked with a QC strain and this spiked sample is then processed through the test method. A positive result from the spiked sample validates the testing method. The QC strains are also used to quality control media that is used to grow microorganisms. The media is inoculated with the QC strain and the growth is observed.

Traditionally these quality control checks that are performed with QC strains are qualitative. Recently, however, regulatory authorities such as ISO have begun enforcing quantitative quality control checks.

One problem that microbiology laboratories face is the issue of cross contamination. Laboratories can inadvertently contaminate a real sample with a QC strain. This results in a false positive result, which can have enormous implications such as unnecessary product recalls or incorrect diagnosis of disease.

In order to help with identifying instances of cross contamination, laboratories try to use species of bacteria as QC strains that are rarely detected in their samples. For example, in Australia *Salmonella salford* is used as a QC strain because it is rarely detected in clinical, food or environmental samples. When a laboratory detects *Salmonella*, tests are performed to check that the *Salmonella* detected is not *Salmonella salford*. If it does prove to be *Salmonella salford* then the validity of the result is questioned.

The use of rare species such as *Salmonella salford* as QC stains does help to identify cross contamination problems, however, confirming the identity of the strain that has been detected takes time. Typically, this confirmation takes between one and three days. In some instances, the confirmation has to be performed by a specialist laboratory. These lengthy delays can have serious implications. For example, a product recall may be delayed for several days during which time consumers would be exposed to the risk of infection.

A further problem with the use of rare species as QC strains is that the rare species may have biochemical or physiological properties that are different to those of the commonly isolated organisms. For example, *Salmonella salford* does not grow well on some media that are routinely used to isolate *Salmonella* from food, whereas the commonly isolated *Salmonella* such as *Salmonella typhimurium* do grow well on these media. *Salmonella salford* is therefore not a suitable QC strain for these culture media.

In an attempt to address this problem, the present inventors hypothesized that it would be extremely useful to have QC microorganisms that form colonies on agar plates are fluorescent when viewed by the naked eye with illumination from a UV lamp.

The genetic modification of microorganisms with fluorescent genes has been widely studied (GFP: Properties, Applications, and Protocols (1998) Chalfie M, Kain S. Wiley-Liss, New York, USA). The most commonly employed gene for a fluorescent protein is the green fluorescent protein (GFP) gene (gfp) from the jellyfish *Aequorea victoria*. Genes encoding other fluorescent proteins have also been isolated from other coelenterates.

Fluorescent bacteria have been created previously by incorporating a gfp gene into a plasmid and inserting the plasmid into the bacteria. The plasmid normally contains an antibiotic resistant gene that allows the bacteria to be grown on antibiotic containing media. The antibiotics kill any bacteria that do not retain the plasmid. These plasmid-containing strains only retain their fluorescence when grown on media that contain antibiotics.

An advantage of plasmid-carrying strains is that several hundred copies of the plasmid are normally present within a bacterial single cell. This means that several hundred copies of the fluorescence gene can be placed within each cell to create cells that are very fluorescent.

Plasmid instability can be a major problem in culturing bacteria, particularly if the cultures go through many generations by passaging. The resulting effects are loss of expression of any plasmid-encoded phenotype because of the build-up of non-productive plasmid-free cells. Plasmid instability can be due to segregational instability and/or structural instability. Segregational instability is the loss of plasmid from one of the daughter cells during cell division because of defective partitioning. Structural instability is attributed to deletions, insertions and rearrangements in the plasmid DNA, resulting in the loss of expression of the encoded phenotype. Plasmid stability is influenced by the vector and host genotypes, vector copy number, and the origin and size of foreign DNA have been observed to affect plasmid stability. Plasmid stability is also a function of physiological parameters that affect the growth rate of the host cell, which include pH, temperature, aeration rate, medium components and heterologous protein accumulation.

Plasmid instability is undesirable in the production of bacterial strains for quantitative QC methods, as consistent expression of the QC phenotype is paramount. Consistent expression could be achieved by irreversibly integrating the genes encoding the fluorescent phenotype into the host genome to ensure long-term stability and expression of the gene product. Ideally, only a single copy of the marker gene should be integrated into the bacterial chromosome as this reduces the likelihood of gene instability resulting from homologous recombination-mediated gene excision.

The preferred requirement of a single copy fluorescence gene in the bacterial genome means that achieving sufficient fluorescence maybe challenging. In comparison, the use of a plasmid containing strain allows several hundred copies of the fluorescence gene to be present. To ensure that a high level of fluorescence is achieved with a single copy on the genome a transcriptional promoter should be chosen that is powerful enough to produce visible fluorescence.

It has been found to be difficult to incorporate genes into a bacterial chromosome and still obtain the required selective or characteristic genotype.

The present inventors have developed several strong bacterial promoter systems for the expression of fluorescent phenotypic markers in microbial cells.

SUMMARY OF INVENTION

The present inventors have devised methods which surprisingly allow for the preparation of microorganisms that are fluorescent even when passaged multiple times on media that does not contain antibiotics or other selective pressures.

In a first aspect, the present invention provides an isolated mutated green fluorescent protein (gfp) gene for insertion into the chromosome of a bacterium, the gene is capable of being expressed and produce sufficient fluorescence under illumination from a UV lamp in a bacterial colony to be seen by the naked eye.

Mutations at nucleotides positions 1492, 1493 (Ser72Ala), 1737 (Met153Thr) and 1766 (Val163Ala), as set out in FIG. 3, in the wild-type gfp gene, or mutations for synonymous codons which change the same amino acid positions (Ser72Ala, Met153Thr and Val163Ala), are encompassed by the present invention.

In a preferred form, the mutated gfp gene has a nucleic acid sequence from bases 1524 to 2240 as set out in FIG. 4 (SEQ ID NO 6).

The mutated gene can be preferably optimized for different bacteria. The gene is particularly adapted for chromosomal insertion and expression in bacteria.

In a second aspect, the present invention provides an isolated green fluorescent protein (GFP) expressed by the mutated gfp gene according to the first aspect of the present invention.

In a third aspect, the present invention provides an isolated mutant green fluorescent protein (GFP) capable of producing sufficient fluorescence under illumination from a UV lamp in a bacterial colony to be seen by the naked eye.

Preferably, the isolated mutant GFP is selected from a protein having one or more mutations of mutant GFP01, mutant GFP02, mutant GFP03, mutant GFP07, mutant GFP10, mutant GFP15, mutant GFP16, mutant GFP20, mutant GFP21, mutant GFP22, mutant GFP26, mutant GFP27, mutant GFP37, mutant GFP43, mutant GFP44, mutant GFP53, mutant GFP54, or mutant GFP55 as defined below in Table 2.

Preferably, the isolated mutant GFP is selected from mutant GFP01, mutant GFP02, mutant GFP03, mutant GFP07, mutant GFP10, mutant GFP15, mutant GFP16, mutant GFP20, mutant GFP21, mutant GFP22, mutant GFP26, mutant GFP27, mutant GFP37, mutant GFP43, mutant GFP44, mutant GFP53, mutant GFP54, or mutant GFP55 as defined below in Table 2.

In a preferred from, the isolated mutant GFP has an amino acid sequence as set out in SEQ ID NO 4.

In a fourth aspect, the present invention provides an unrepressed or constitutive gene cassette for providing a gene to a chromosome comprising an endogenous gene under the control of the very strong bacteriophage lambda promoter left ($P_L$) and one or more transposon elements. It will be appreciated that the cassette can incorporate other suitable transcriptional promoters to allow expression of a gene product in a cell or bacterium.

In one form, the cassette has a nucleotide sequence from 1 to 1278 and 1996 to 2007 substantially as shown in FIG. 3, wherein the gene is inserted between positions 1728 and 1996.

In another form, the cassette has a nucleotide sequence from 1 to 1523 and 2241 to 2326 substantially as shown in FIG. 4 (SEQ ID NO 4), wherein the gene is inserted between positions 1523 and 2241.

In a preferred form, the cassette has a nucleotide sequence from 1 to 309 and 1027 to 1032 substantially as shown in FIG. 5 (SEQ ID NO 7), wherein the gene is inserted between positions 310 and 1026 (SEQ ID NO 8).

The cassette is suitable of inserting any gene, endogenous or exogenous, mutant or native into the chromosome of a bacterium or cell. Examples include but not limited to genes encoding green fluorescent protein (gfp), red fluorescent protein, yellow fluorescent protein or any unmodified or modified versions of known fluorescent proteins. Examples also include genes that encode proteins capable of catalysing the production of colorimetric or fluorescent pigments, including but not limited to carotenoids, indole or indirubin.

Preferably, the gene is a green fluorescent protein (gfp) gene. More preferably, the gene is a mutant gfp gene.

The present inventors have demonstrated the suitability of the cassette by developing bacteria having enhanced fluorescence by inserting a green fluorescent protein (gfp) gene into the chromosome of the bacteria. It will be appreciated that the cassette can be used for any suitable gene to allow expression of the gene product in a cell or bacterium.

In a fifth aspect, the present invention provides a bacterium or cell containing a gene cassette according to the fourth aspect of the present invention.

In a sixth aspect, the present invention provides an unrepressed or constitutive gene cassette for providing a green fluorescent protein (gfp) gene to a bacterium comprising a gfp gene under the control of a strong promoter and one or more transposon elements.

Preferably, the gene is under the control of the very strong bacteriophage lambda promoter left ($P_L$).

In one form, the cassette is substantially as shown in FIG. 3 (SEQ ID NO 1).

In another form, the cassette is substantially as shown in FIG. 4 (SEQ ID NO 4).

Preferably, the cassette is as substantially as defined in FIG. 5 (SEQ ID NO 7).

In a preferred form, the mutant gfp gene substantially as shown in nucleotide bases 310 to 1026 of FIG. 5 (nucleotide bases 310 to 1026 of SEQ ID NO 7).

The cassette is particularly suitable for providing a mutant green fluorescent protein to the chromosome of a bacterium.

It will be appreciated that similar results could be achieved with other forms of GFP, possibly even the wild type GFP would be sufficiently fluorescent when used with the gene cassette according to the present invention.

In a seventh aspect, the present invention provides a bacterium or cell containing the mutated GFP gene according to the first aspect of the present invention or a gene cassette according to the fourth aspect of the present invention.

The bacterium can be any suitable bacterium such as *Acinetobacter lwoffii, Aeromonas hydrophila, Aspergillus niger, Bacillus cereus, Bacillus subtilis, Campylobacter coli, Campylobacter jejuni, Candida albicans, Citrobacter freundii, Clostridium perfringens, Clostridium sporogenes, Edwardsiella tarda, Enterobacter aerogenes, Enterobacter cloacae, Enterococcus faecalis, Escherichia coli, Escherichia coli* O157, *Haemophilus influenzae, Klebsiella pneumoniae, Klebsiella aerogenes, Lactobacillus acidophilus, Lactobacillus casei, Lactobacillus fermentus, Legionella pneumophila, Listeria innocua, Listeria ivanovii, Listeria monocytogenes,* Meth. Resist. Staph. Aureus, *Neisseria gonorrhoeae, Proteus rettgeri, Proteus mirabilis, Proteus vulgaris, Pseudomonas aeruginosa, Pseudomonas cepacia, Pseudomonas fluorescens, Rhodococcus equi, Salmonella abaetetuba, Saccharomyces cerevisiae, Salmonella salford, Salmonella menston, Salmonella sofia, Salmonella Poona, Salmonella typhimurium, Salmonella poona, Serratia marcescens, Shigella sonnei, Staphylococcus aureus, Staphylococcus epidermidis, Streptococcus pneumoniae, Streptococcus pyogenes, Vibrio parahaemolyticus, Yersinia enterocolitica, Zygosaccharomyces rouxii.*

Preferably, the bacterium is *Escherichia coli*. More preferably, the *E. coli* is NCTC 9001 or NCTC 12241 as herein defined.

Preferably, the bacterium is *Salmonella* sp. More preferably, the *Salmonella* sp is *Salmonella typhimurium* or *Salmonella abaetetuba* as herein defined.

Preferably, the bacterium is *Listeria* sp. More preferably, the *Listeria* sp is *L. monocytogenes*.

Examples of bacteria containing a mutated GFP gene or cassette according to the present invention have been deposited with the National Measurement Institute (formerly Australian Government Analytical Laboratories), PO Box 385, Pymble NSW 2073, Australia, on 13 Sep. 2004 under Accession Nos NM04/42817, NM04/42818, NM04/42819 and NM04/42820.

The identity of the deposited bacteria are as follows:
NM04/42817 is *E. coli* NCTC12241
NM04/42818 is *Salmonella abaetetuba*
NM04/42819 is *Salmonella typhimurium*
NM04/42820 is *E. coli* NCTC9001

The cell can be any suitable cell including prokaryotic or eukaryotic. Examples of non-bacterial cells include fungal and yeast cells such as *Candida albicans, Zygosaccharomyces rouxii* or *Aspergillus niger*.

In a eighth aspect, the present invention provides a modified bacterium containing a mutated gfp gene or cassette selected from NM04/42817, NM04/42818, NM04/42819 or NM04/42820.

In a ninth aspect, the present invention provides use of a bacterium according to the seventh or eighth aspects of the present invention having fluorescence as a detectable marker.

Preferably, the use is as a laboratory QC strain.

The fluorescent bacteria are suitable for use as internal quality controls as described in WO 01/09281, incorporated herein by reference.

The fluorescent bacteria can be used for tracking purposes. Examples of this use include: studies on the transport of cells within the environment; tracking of cells within water treatment plants; studies on gene exchange in the environment.

The fluorescent bacteria can be used to leak test biological safety equipment such as safety cabinets and respirators.

The fluorescent bacteria can be used to test the efficiency of any process that is designed to remove or inactivate bacteria. Examples include water filters, UV disinfection methods, chemical disinfection methods and heat treatment.

The fluorescent bacteria are also suitable for use in materials testing methods. Examples of this include the testing of water fittings to show that they do not support the growth of microorganisms.

The fluorescent bacteria are suitable for use in a sewage treatment process. Sewage treatment relies on the presence of specific bacteria such as nitrifying bacteria. Adding fluorescent nitrifying bacteria would allow accurate monitoring of cell density of nitrifying bacteria within the sewage treatment process.

Bacteria are commonly used to control non-desirable bacteria. Bacteria are added to a process or a product to outcompete non-desirable bacteria. An example of this is the control of *Salmonella* on chickens. Chickens are routinely treated with *Salmonella* cells from a specific strain of *Salmonella*, known as *Salmonella sofia*, that is not infectious to humans. The *Salmonella sofia* colonises the chickens and out-competes more harmful strains of *Salmonella*. At present there is not a simple method to check that the chickens are colonised with *Salmonella sofia*. By treating the chickens with a fluorescent form of *Salmonella sofia* the level of *Salmonella sofia* on a chicken or on processed chicken meat could be easily monitored by measuring fluorescence. Fluorescence bacteria could be used for any process that requires the monitoring of introduced bacteria.

The bacterium can be supplied as a culture or in the form of a BioBall™ (BTF Pty Ltd, Australia) according to U.S. Pat. No. 6,780,581 or WO 03/020959.

The present inventors have found that the fluorescence is substantially stable when the bacteria are passaged multiple times. Antibiotics, for example, are not required to keep the fluorescence gene within the bacteria.

The mutated GFP gene results in brighter fluorescence in *E. coli*, for example, compared with a wildtype GFP gene expressed in a plasmid in an equivalent strain of *E. coli*. Not being bound by theory, the inventors believe that brighter fluorescence may be due to rapid maturation of the green fluorescence protein in bacteria. As the mutations have slightly changed the structure of the protein, it is likely that this changed structure matures more rapidly in bacteria than the wild type GFP.

Although other mutants of the GFP gene have been made and disclosed in the prior art, all these mutants have fluorescence excitation and emission properties different to the wild type GFP. The GFP mutant according to the present invention, however, has substantially the same excitation and emission spectra as the wild type GFP.

Although other forms of tagging bacteria on the chromosome have been published previously, the tagging methods enable the bacteria to grow on certain media or selective conditions.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia prior to development of the present invention.

In order that the present invention may be more clearly understood, preferred embodiments will be described with reference to the following drawings and examples.

BRIEF DESCRIPTION OF THE DRAWINGS

FIG. 3 shows a sequence map of the gfp gene cassette (SEQ ID NO 1) containing the wild-type gfp gene, showing the location of the major sequence elements as depicted in FIG. 1D. Key restriction sites are underlined. The lambda $P_R$ operators are underlined and marked R1-R3. The lambda $P_L$ operators are underlined and marked L1-L3. A translation of the lambda $cI^{ts857}$ gene is shown underneath the DNA sequence (running in reverse orientation 17 to 730 bp SEQ ID NO 2). A translation of the gfp gene is shown underneath the DNA sequence (running in forward orientation 1279 to 1995 bp; SEQ ID NO 3).

FIG. 4 shows a sequence map of the gfp gene cassette (SEQ ID NO 4) containing the modified gfp gene, after deletion of the lambda $cI^{ts857}$ gene and lambda $P_R$ promoter. Key restriction sites are italicised. The lambda $P_L$ operators are underlined and marked L1-L3. Transposon arms are underlined (6-54 bp and 2273-2321 bp). Codons changed by site directed mutagenesis to generate the modified gfp gene are underlined and labelled. A translation of the chloramphenicol resistance gene is shown underneath the DNA sequence (278 to 937 bp; SEQ ID NO 5). A translation of the modified gfp gene is shown underneath the DNA sequence (1524 to 2240 bp; SEQ ID NO 6).

FIG. 5 shows a sequence map of the minimal gfp gene cassette (SEQ ID NO 7) containing the modified gfp gene and lambda $P_L$ promoter. Key restriction sites are italicised. The lambda $P_L$ operators are underlined and marked L1-L3. Codons changed by site directed mutagenesis to generate the modified gfp gene are underlined and labelled. A translation of the modified gfp gene is shown underneath the DNA sequence (310 to 1026 bp; SEQ ID NO 8).

MODE(S) FOR CARRYING OUT THE INVENTION

Example 1

The following example describes the creation of a GFP cassette, the creation of mutants of GFP that showed increased fluorescence in a plasmid within *E. coli* and the chromosomal integration of the mutant GFP and the wild type GFP into *E. coli*.
Construction of a Temperature Controlled GFP Gene Cassette In an attempt to obtain visibly detectable levels of GFP in bacterial colonies, a gene cassette was constructed comprising a modified gfp gene under the control of the very strong bacteriophage lambda promoters right and left ($P_R$ and $P_L$), and the gene coding for lambda thermolabile $cI^{ts857}$ repressor protein. The regulatory regions for the gfp gene cassette were obtained from the controlled expression vector pJLA602 (Schauder et al., 1987 Gene 52: 279-283) by PCR. The $cI^{ts857}$ repressor protein tightly represses transcription from the lambda $P_R$ and $P_L$ promoters when grown at temperatures below 37° C. Incubating growing cultures at 42° C. results in inactivation of the $cI^{ts857}$ repressor protein resulting in high level transcription of genes placed immediately downstream of the lambda $P_L$ promoter.

Figure 1:
FIG. 1. A. Diagrammatic representation of oligonucleotide primer binding positions relative to the proposed gfp gene cassette. B. Diagrammatic representation of the two PCR products generated with oligonucleotide primer pairs as marked, for construction of the gfp gene cassette, containing the wild-type gfp gene, by overlap extension PCR. C. Diagrammatic representation of the five PCR products generated with oligonucleotide primer pairs as marked, for construction of the complete gfp gene cassette, containing modified gfp genes, by overlap extension PCR. D. Diagrammatic representation of the structure of the gfp gene cassette showing the position and orientation of the clts857 and gfp genes, and the positions of the lambda $P_R$ and $P_L$ operators. The relative positions of the codons within gfp that are altered by site directed mutagenesis are marked by their corresponding amino acid changes.
Figure 1:
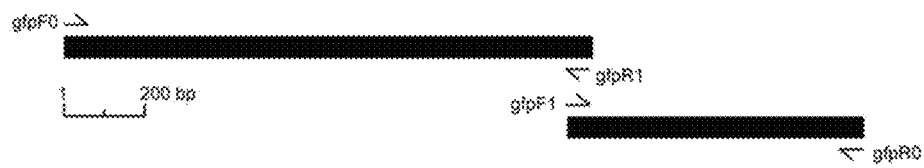
Figure 1:
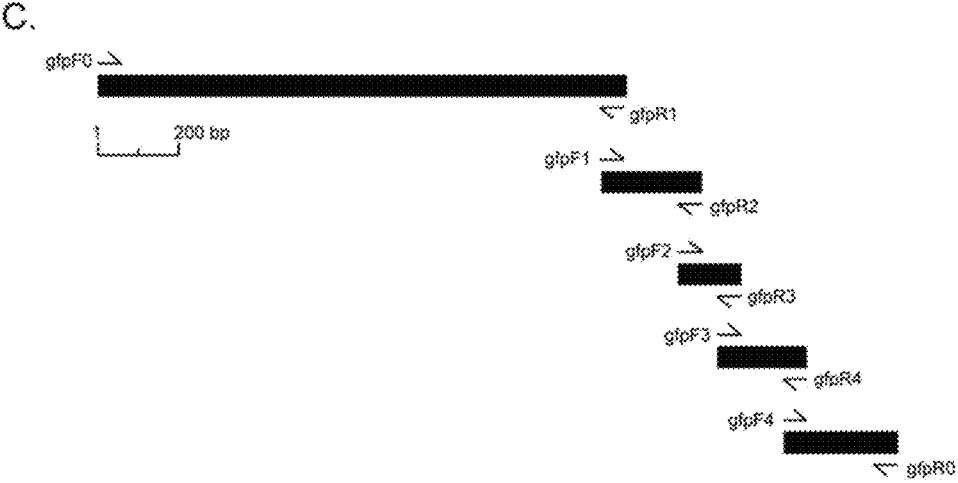
Figure 1:
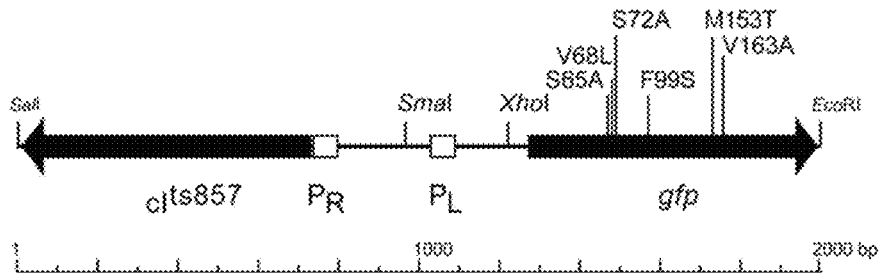

The modified gfp gene was constructed by site directed mutagenesis using overlapping sets of degenerate oligonucleotides to reconstruct the full length gfp gene with 6 modified codons positions. The modified sites and the selected residue alterations were chosen for their proven ability to improve the maturation and fluorescence of GFP in *E. coli*. The use of degenerate oligonucleotide primers resulted in the creation of a library of gfp genes that varied between 2 or 3 possible codons at each of the 6 chosen codon positions. The oligonucleotide primers are described below and are listed in Table 1. The binding positions of all oligonucleotide primers with respect to the gfp cassette are shown in FIG. 1A. The PCR products generated with said primers for reconstruction of the gfp cassette is shown in FIG. 1C. The complete gfp cassette is shown in FIG. 1D. The wild-type gfp gene was also placed into the cassette in the same manner for use as a control (see FIG. 1B).

TABLE 1

| Name | Sequence | SEQ ID NO |
|---|---|---|
| gfpF0 | 5'-TTTTTTGAATTCTTATTTGTATAGTTCATC | 9 |
| gfpR1 | 5'-CTTTACTCATGGCAGTCTCCAGTTTGT | 10 |
| gfpF1 | 5'-GAGACTGCCATGAGTAAAGGAGAAGA | 11 |
| gfpF2 | 5'-ATGGTSTTCAATGCTTTKCRAGATACCCAGATCATA | 12 |
| gfpF3 | 5'-AACTATATYTTTCAAAGATGACGGGA | 13 |
| gfpF4 | 5'-CAAACAAAAGAATGGAATCAAAGYTAACTTCAAAATTAGA | 14 |
| gfpR0 | 5'-TTTTTTGAATTCTTATTTGTATAGTTCATC | 15 |

TABLE 1-continued

| Name | Sequence | SEQ ID NO |
|---|---|---|
| gfpR2 | 5'-AAAGCATTGAASACCATAMSMGAAAGTAGTGACAAGT | 16 |
| gfpR3 | 5'-CTTTGAAARATATAGTTCTTTCCTGTA | 17 |
| gfpR4 | 5'-TTCCATTCTTTTGTTTGTCTGCCRTGATGTATACATTGTGT | 18 |
| gfpEnt | 5'-CCAGTTTGCTCAGGCTCT | 19 |
| T7promppf1 | 5'-GGGGAATTCTTAATACGACTCACTATAGAAGGAGATATACATAT GGCCTCCGAGAACGTCATCA | 20 |
| Rfppr1 | 5'-GGGGGGGTCGACCTACAGGAACAGGTGGTGG | 21 |
| PENTGWF | 5'-TGATCTTCCGTCACAGGT | 22 |
| GFPGWR | 5'-GTAACAGCTGCTGGGATT | 23 |

The oligonucleotides primers used for the PCR amplification of the gfp gene cassette regulatory regions were as follows:
gfpF0, 5'-TTTTTTGAATTCTTATTTGTATAGTTCATC-3' (SEQ ID NO 9), a primer to amplify bacteriophage lambda cl$^{ts857}$/P$_R$/P$_L$ region from pJLA602. This primer incorporates a SalI site for directional ligation of the cassette into a plasmid vector.
gfpR1, 5'-CTTTACTCATGGCAGTCTCCAGTTTGT-3' (SEQ ID NO 10), a primer to amplify and overlap the lambda cl$^{ts857}$ repressor gene/P$_R$/P$_L$ with the gfp gene.

Variants of the GFP were generated by oligonucleotide directed mutagenesis of the wild type gfp gene. Mutagenic PCR amplifications of the GFP gene were performed using combinations of degenerate and non-degenerate oligonucleotide primers.

For the site directed mutagenesis and PCR amplification of the gfp gene the following oligonucleotides were used:
gfpF1,5'-GAGACTGCCATGAGTAAAGGAGAAGA-3' (SEQ ID NO 11), a primer to amplify and overlap lambda cl$^{ts857}$/P$_R$/P$_L$/atpE with the gfp gene.
gfpF2,5'-ATGGTSTTCAATGCTTTKCRAGATAC-CCAGATCATA-3' (SEQ ID NO 12), a degenerate primer for the amplification and mutagenesis of gfp. This primer introduces three possible point mutations, Ser65Ala or Ser65Gly, Val68Leu, and Ser72Ala into the gfp gene.
gfpF3,5'-AACTATATYTTTCAAAGATGACGGGA-3' (SEQ ID NO 13), a degenerate primer for the amplification and mutagenesis of gfp. This primer introduces a single possible point mutation, Phe99Ser, into the gfp gene.
gfpF4,5'-CAAACAAAAGAATGGAAT-CAAAGYTAACTTCAAAATTAGA-3' (SEQ ID NO 14), a degenerate primer for amplification and mutagenesis of gfp. This primer introduces a single possible point mutation, Met153Thr, into the gfp gene.
gfpR0 primer 5' TTTTTTGAATTCTTATTTGTATAGT-TCATC-3' (SEQ ID NO 15), a primer to amplify the gfp gene. This primer incorporates an EcoRI restriction site for directional ligation of the cassette into a plasmid vector.
gfpR2,5'-AAAGCATTGAASACCATAMSMGAAAG-TAGTGACAAGT-3'(SEQ ID NO 16), a degenerate primer for the amplification and mutagenesis of the gfp gene. This primer introduces two possible point mutations, Ser65Ala or Ser65Gly and Val68Leu, into the gfp gene.
gfpR3 primer 5'-CTTTGAAARATATAGTTCTTTCCT-GTA-3' (SEQ ID NO 17), a degenerate primer for amplification and mutagenesis of the gfp gene. This primer introduces a single possible point mutation, Phe100Ser, into the gfp gene.
gfpR4 primer 5'-TTCCATTCTTTTGTTTGTCTGCCRT-GATGTATACATTGTGT-3' (SEQ ID NO 18), a degenerate primer for amplification and mutagenesis of the gfp gene. This primer introduces a single possible point mutation, Met153Thr, into the gfp gene.

For amplification and mutagenesis of the gfp gene, plasmid DNA from the pGFP vector (Clontech) was used as template DNA. PCR amplification of the gfp gene, the regulatory regions and the gfp gene segments contained 1×PCR Gene Amp buffer; 200 µM of each of the four deoxyribonucleotide triphosphate (dATP, dTTP, dCTP, dGTP); 0.3 µM of each oligonucleotide primer (forward and reverse); AmpliTaq-Gold Polymerase (Applied Biosystems) and approximately 10 ng of template DNA in a 50 µl reaction volume. PCR reactions were performed in a Gene Amp PCR system 2400 (Applied Biosystems) programmed as follows: 95° C. for 10 min, (95° C. 30 sec, 55° C. 30 sec, 72° C. 1 min) repeated for 30 cycles, and a final cycle at 72° C. for 5 min. PCR products originating from amplification reactions of the regulatory regions and the four different segments of the mutant gfp gene were visualized by agarose gel electrophoresis and the DNA purified using a QIAquick gel extraction kit (Qiagen Inc).

Assembly of the gfp gene and regulatory regions into the gfp gene cassette were performed by overlap extension PCR (Ho et al., 1989 Gene 77:51-59). Optimization of PCR conditions was required for successful assembly of the gfp gene cassette. Best results for the assembly of gfp gene segments into an full length gene were obtained by first performing a primerless overlap extension step with a programmed decrease in the annealing temperature (1° C. per PCR cycle) followed by addition of oligonucleotides and a further PCR step. The PCR reagents used were the same as that described above, except for combining and using the 4 gfp gene cassette segments, each at approximately 10 ng, as template DNA in a 50 µl PCR reaction. The relative positions of primers with respect to the major elements in the GFP cassette are shown in FIG. 1A. The relative positions of PCR products amplified and used for overlap extension reassembly of the GFP cassette are shown in FIG. 1B. The final complete GFP cassette is depicted in FIG. 1C.

A PCR for the assembly of the wild type gfp gene and the upstream lambda regulatory regions into a single cassette was performed as follows: a primerless overlap extension stage (95° C. for 10 min, 95° C. 30 sec, 50° C. down to 35° C. over 15 cycles with 1° C. decrease per cycle for 30 sec each cycle), followed by addition of primers (gfpF0 and gfpR0) and a second PCR stage comprising 95° C.-30 sec, 55° C.-30 sec, 72° C.-1 min, repeated for 30 cycles, and a final cycle at 72° C. for 5 min.

A PCR for the recombination of the four mutant GFP gene segments into a pool of selectively mutated full length gfp genes was as follows: a primerless overlap extension stage (95° C. for 10 min, 95° C. 30 sec, 50° C. down to 30° C. over 20 cycles with 1° C. decrease per cycle for 30 sec each cycle), followed by addition of primers (gfpF1 and gfpR0) and a second PCR stage of 95° C. 30 sec, 55° C. 30 sec, 72° C. 1 min, repeated for 30 cycles. After amplifying the assembled mutant gfp gene, a second PCR reaction was carried out using the same conditions used for the assembly of the wild type gfp gene, but in this case using the reassembled mutant gfp gene and the upstream regulatory regions to reassemble the entire mutant gfp gene cassette.

The complete sequence of the mutated gfp gene cassette, including gene translations, promoter elements, and mutation positions, is given in FIG. 3. Similarly, The complete sequence of the wild-type gfp gene cassette is given in FIG. 4.
Creation of GFP Mutants The gfp gene cassette was designed to include two unique restriction enzyme sites, SalI at the 5' end and EcoRI at 3' end. These restriction sites were used for direction ligation of the mutated gfp gene cassette into the multiple cloning site of the pEntranceposon CmR vector (Finnzymes). The pEntranceposon CmR vector is a high copy number plasmid constructed by replacing the multiple cloning site of the high copy number plasmid pUC19 with the bacterial phage Mu transposon, and the chloramphenicol resistance gene (CamR).

PCR product comprising the complete mutant gfp gene and the plasmid vector pEntranceposon CamR were digested with SalI and EcoRI restriction enzymes (MBI Fermentas). The digested DNA fragments were visualized and purified from agarose gel using a QIAquick gel Extraction kit (Qiagen). The digested mutated gfp gene cassette and pEntranceposon CamR vector were ligated together and transformed into *E. coli* DH5α to generate a library of clones containing gfp genes randomly mutated at 6 selected positions (see FIG. 2). Similarly, the wild type GFP gene cassette was ligated to the digested pEntranceposon CamR vector and transformed into *E. coli* DH5 alpha.

Transformed cells were plated onto Luria Bertani (LB) agar media plates containing 25 µg/ml of chloramphenicol and incubated at 28° C. After 48 hours incubation, the incubation temperature was shifted to 42° C. for two to three hours for inactivation of the $cI^{ts857}$ repressor protein and induction of GFP expression. Colonies expressing GFP were screened by visualization of fluorescence using a hand held ultraviolet lamp (UV 365 nm). A number of colonies expressing GFP appeared on the plates. Colonies originating from the mutant GFP gene construct showed visually detectable variation in GFP fluorescence intensity emitted from colonies and were graded accordingly.

Sequencing the Mutant GFP Clones

Five wild type GFP transformants and 18 mutant GFP transformants were selected following visual screening for fluorescence. Several of the mutant GFP transformants were significantly brighter than the wild type GFP transformants. The selected mutant GFP clones included the brightest fluorescing colonies as well as colonies showing intermediate and low intensity fluorescence. Single recombinant colonies were re-streaked to new LB plates containing 25 µg/ml of chloramphenicol. These cells were used for inoculation of 3 ml LB liquid media containing 25 µg/ml of chloramphenicol. Cultures obtained after overnight incubation at 28° C. with shaking were used for plasmid DNA extraction using QIAprep kits (Qiagen). Extracted plasmid DNA from the selected GFP clones was then used for nucleotide sequencing of the gfp gene cassette to determine the gfp genotype. Sequencing reactions (Big Dye terminator chemistry Applied Biosystems Inc) were performed using plasmid DNA extracted from GFP transformants. The oligonucleotide primers gfpF0 and gfpR1 were used for sequencing of the regulatory regions of GFP gene cassette, while gfpF1 and gfpR0 primers for sequencing of the GFP gene open reading frame within the GFP gene cassette. Sequencing results were analyzed using the GCG Wisconsin software package version 8 (Devereux J, Haeberli P, Smithies O, 1984, Nucleic Acids Res 12:387-395). Results from the nucleotide sequencing analysis were used for amino acid sequence alignment of wild type GFP and GFP mutants. A summary of amino acid changes identified in the GFP mutants is presented in Table 2.

Results from the sequencing analysis indicated that the most frequently occurring amino acid changes, Ser at position 72 to Ala, Met at position 153 to Thr and Val at position 163 to Ala, were found in the GFP mutants clones showing the brightest fluorescence intensity when visualized as colonies on plates illuminated with ultraviolet light (UV 365 nm). These mutants were considerably brighter than colonies that contained the wild type GFP.

The mutant gfp gene construct containing the three most frequent amino acid changes as well as wild type GFP gene construct were chosen for bacterial chromosomal integration experiments as described below. This plasmid was named pENTclGFP (See FIG. 2B).

TABLE 2

| | Modified amino acid residues | | | | | |
|---|---|---|---|---|---|---|
| | Position | | | | | |
| | 65 | 68 | 72 | 99 | 153 | 163 |
| wild type GFP | Ser | Val | Ser | Phe | Met | Val |
| mutant GFP01 | Ser | Val | Ala | Phe | Thr | Ala |
| mutant GFP02 | Ala | Val | Ala | Phe | Thr | Ala |
| mutant GFP03 | Ser | Val | Ser | Phe | Thr | Ala |
| mutant GFP07 | Ser | Val | Ala | Phe | Thr | Ala |
| mutant GFP10 | Ser | Val | Ser | Phe | Thr | Ala |
| mutant GFP15 | Ser | Val | Ala | Phe | Thr | Ala |
| mutant GFP16 | Ser | Leu | Ala | Phe | Thr | Ala |
| mutant GFP20 | Ser | Val | Ala | Phe | Thr | Ala |
| mutant GFP21 | Ser | Leu | Ala | Phe | Thr | Ala |
| mutant GFP22 | Ser | Val | Ser | Phe | Met | Ala |
| mutant GFP26 | Ser | Leu | Ala | Phe | Thr | Ala |
| mutant GFP27 | Ser | Leu | Ala | Ser | Met | Ala |
| mutant GFP37 | Ser | Val | Ala | Phe | Thr | Ala |
| mutant GFP43 | Ser | Val | Ser | Phe | Thr | Ala |
| mutant GFP44 | Ser | Leu | Ala | Ser | Thr | Ala |
| mutant GFP53 | Ser | Leu | Ala | Ser | Met | Ala |
| mutant GFP54 | Ser | Val | Ser | Ser | Met | Val |
| mutant GFP55 | Ser | Val | Ser | Ser | Thr | Val |

Integration of GFP into the Chromosome of *E. coli*

Integration of the gfp gene cassette into the *E. coli* DH5α genome was performed by insertion mutagenesis using bacteriophage Mu DNA transposition complexes (Lamberg et al., 2002 Appl Environ Microbiol 68: 705-712). This system was chosen as the transposon cassette does not include the gene encoding Mu transposase. Transposase enzyme is added to purified transposon DNA to form a transposition complex that is then transferred into bacterial cells by electroporation. The transposase mediates the integration of the transposon into the genome, effectively resulting in irreversible integration of the transposon and any included genes, into the bacterial chromosome.

Plasmid DNA of pEntranceposon vectors containing the GFP gene cassette were used for BglII restriction enzyme digests. The BglII digestion excises the transposon from the pEntranceposon vector. Digested plasmid DNA was separated using agarose gel electrophoresis and the pEntranceposon CamR transposon fragment containing the gfp gene cassette purified using a QIAquick gel Extraction kit (Qiagen Inc). Purified pEntranceposon DNA was used for transpososome assembly reactions.

Transpososomes are stable protein DNA complexes formed by the binding of MuA transposase protein into specific binding sites at each end of the transposon DNA.

Transpososome formation reactions were optimized by titration of the amount of pEntranceposon DNA against a fixed amount of MuA transposase enzyme (Finnzymes). Reagents for transpososome assembly reaction mixtures (20 µl) included ~6 pmol of MuA transposase, 50% glycerol, 150 mM of Tris-HCl (pH 6.0), 150 mM NaCl, 0.1 mM EDTA, and 0.025% (v/v) Triton X-100. Transpososome reactions were performed by adding ~0.25 pmol to ~1.0 pmol of pEntranceposon DNA containing the GFP gene cassette to the mixtures followed by incubating at 30° C. for 2-3 hours. Transpososome formation was visualized by electrophoresis on 2% agarose-TAE buffer gel containing 80 µg/ml of bovine serum albumen. Transpososome assembly reaction samples (1 µl) were loaded into the gel using 0.2 (v/v) of Ficoll 400 as loading buffer. After gel visualization, selected transpososome complexes were used for the transformation of electrocompetent E. coli DH5α cells.

Electrocompetent E. coli cells were prepared by growing 500 ml of culture in SOB medium at 37° C. with shaking to optical density at 600 nm of 0.8. Cells were then harvested by centrifugation at 4° C. and resuspended in 25 ml of ice-cold 10% glycerol four times consecutively, then resuspended in 1 ml of ice-cold 10% glycerol. Aliquots of 1 µl of transpososome reactions were used for electroporation of 40 µl electrocompetent E. coli cells using a Genepulser (Bio-Rad) at the following settings: voltage 2.5 kV; capacitance 25 µF; resistance 200Ω (Bio-Rad 2-mm electrode spacing cuvettes). After electroporation 1 ml of SOC medium was added, incubated for 90 minutes, spread onto LB plates containing 25 µg/ml of chloramphenicol and incubated at 28° C. After 48 hours incubation at 28° C. cultures incubation temperature was shifted to 42° C. for two to three hours to induce GFP expression.

The few colonies that appeared on plates originated from integration of both mutant and wild type GFP gene cassette showed no fluorescence when illuminated with UV lamp. To verify if the integration of the GFP gene cassette was successful, PCR amplification reactions using gfpF1 and gfpR0 primers were carried using colonies growing on plates originating from electro-transformation of both mutant and wild type GFP transpososomes. Results were positive for the presence of the GFP gene in the colonies. Four selected positive colonies (both mutant and wild type GFP putative integrants) were grown overnight in liquid media (LB+chloramphenicol). After harvesting cultures by centrifugation, genomic DNA from ~100 µg of cell paste was extracted using DNA extraction kit (Fast DNA, BIO 101 systems). Genomic DNA from two different isolates originating from both mutant and wild type GFP putative integrants were used for nucleotide sequencing using the system of analysis as described above. Oligonucleotide primers gfpF0 gfpR1 and gfpF1 gfpR0 were used for sequencing of both regulatory and open reading frame within the GFP gene cassette.

The above results confirmed the integration of intact GFP gene cassette sequence in the genomic DNA of the putative integrants. However, they were not visibly fluorescent when grown under inducing conditions. It was considered that this negative result might be due to the single copy nature of the integrated gfp gene in combination with the non-ideal growth temperature when inducing protein production at 42° C. Usually, the lambda $cI^{ts857}/P_R/P_L$ system is used to induce protein production in high copy number plasmid systems, with maximum protein yields usually obtained within 2-3 hours of switching to 42° C. However, with GFP being produced from only a single copy gene we considered that a time potentially much longer than 2-3 hours might be required to achieve visible levels of GFP, and that the 42° C. growth conditions might prevent continued expression of GFP to visible levels. Therefore, we considered that removal of the $cI^{ts857}$ gene and the $P_R$ promoter might allow unrepressed constitutive high-level expression of the GFP protein from the remaining $P_L$ promoter. A simple deletion strategy was devised to test this hypothesis (see Example 2).

Example 2

The temperature inducible gfp gene cassette integrated in E. coli resulted in non-fluorescing colonies. As discussed above, it was considered that a prolonged growth at the 42° C. induction temperature may have inhibited protein production in E. coli before detectable amounts of GFP could be produced from a single copy gfp gene. The following procedure was devised for the deletion of the $cI^{ts857}$ gene from the plasmid to create an unrepressed (constitutively expressed) version of gfp gene cassette.

Generation of Unrepressed gfp Gene Cassette

Analysis of the nucleotide sequence of gfp gene cassette revealed a unique SmaI restriction enzyme that if used in combination with an EcoRV site in the pEntcIGFP plasmid (see FIG. 2C) would result in excision of most of the $cI^{ts857}$ gene and $P_R$ from the cassette. Excision of the $cI^{ts857}$ gene would effectively promote high-level constitutive transcription of gfp from the $P_L$ promoter (see FIGS. 2C and 2D).

The pEntcIGFP plasmid containing the gfp gene cassette was restriction digested with SmaI and EcoRV (MBI Fermentas). The digested DNA was visualized by agarose gel electrophoresis and DNA corresponding to the vector minus excised $cI^{ts857}$ gene was gel purified using a QIAquick gel extraction kit (Qiagen Inc). The digested DNA was ligated blunt-end using T4 DNA ligase (Roche) at 14° C. for 12 hr. The ligated DNA was used to transform chemically competent E. coli DH5 alpha cells, plated onto LB plates containing chloramphenicol and incubated overnight at 37° C. Positive colonies expressing GFP (following visual inspection under UV light) appeared on plates originating from a ligation of the mutant GFP gene cassette with the deleted $cI^{ts857}$ repressor gene. The positive transformants were re-streaked to individual plates and singles colonies used for liquid cultures in LB medium containing chloramphenicol. After incubation overnight at 37° C., an aliquot from the culture was then used for plasmid extraction using QIAprep plasmid purification kit (Qiagen). Excision of the $cI^{ts857}$ gene from the GFP gene cassette was confirmed after analysing an EcoRI restriction enzyme digest of the extracted plasmid by agarose gel electrophoresis. The plasmid containing the GFP gene cassette with the deleted $cI^{ts857}$ gene was named pEntPLGFP, and the modified cassette is from herein referred as unrepressed GFP gene cassette.

Figure 2:
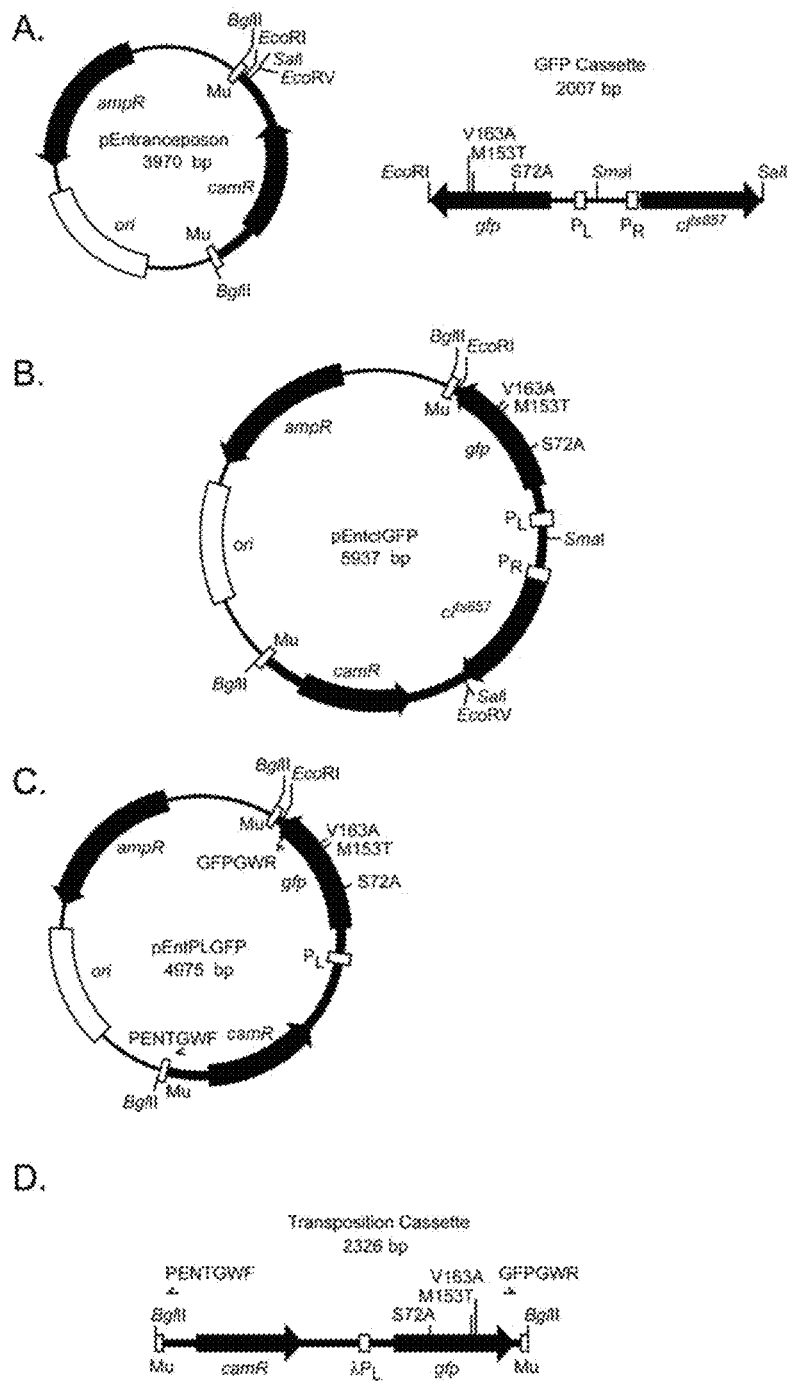
FIG. 2. A. Structure of the pEntransposon-CamR plasmid and the gfp gene cassette. Transposon arms are labeled Mu. The pBR322 origin of replication is labeled ori. B. Structure of the plasmid generated following ligation to the gfp gene cassette into pEntransposon-CamR at EcoRI and SalI restriction sites. Arrows indicate relative binding positions and orientation of oligonucleotides PENTGWF and GFPGWR used for genomic walking PCR. C. Structure of the plasmid shown in B. following deletion of the clts857 gene and the lambda $P_R$ promoter by digestion with EcoRV and SmaI, followed by recircularisation by blunt-end ligation. Arrows indicate relative binding positions and orientation of oligonucleotides PENTGWF and GFPGWR used for genomic walking PCR. D. Structure of the gfp gene cassette once excised from the plasmid shown in C. Arrows indicate relative binding positions and orientation of oligonucleotides PENTGWF and GFPGWR used for genomic walking PCR.

Chromosomal Integration of Unrepressed GFP Gene Cassette into E. coli and Salmonella Strains Bacteriophage Mu DNA transposition complexes derived from pEntPLGFP was used for chromosomal integration of the unrepressed gfp gene cassette into E. coli and Salmonella strains. E. coli DH5 alpha and E. coli NCTC 12241 and E. coli NCTC 9001, and Salmonella typhimurium and Salmonella abaetetuba cells were transformed as follows.

pEntPLGFP plasmid DNA was restriction digested with BglII (see FIG. 2). The resulting two restriction fragments were separated by gel electrophoresis and the DNA fragment comprising the Mu transposon and unrepressed mutant gfp gene cassette purified using a Qiaquick gel extraction kit (Qiagen).

Transpososome assembly reaction mixtures (20 µl) consisted of ~6 pmol of MuA transposase (Finnzymes), 50% glycerol, 150 mM of Tris-HCl (pH 6.0), 150 mM NaCl, 0.1 mM EDTA, and 0.025% (v/v) Triton X-100, and ~0.1 pmol to ~0.9 pmol of pEntranceposon DNA containing the unrepressed gfp gene cassette.

Transpososome formation reactions were incubated at 30° C. for 2-3 hours, visualized on 2% agarose-TAE electrophoresis as described above and used for the transformation of *E. coli* NCTC 12241, *E. coli* NCTC 9001, *Salmonella typhimurium* and *Salmonella abaetetuba* electrocompetent cells. Electrocompetent *E. coli* and *Salmonella* cells were all prepared and electroporated using the method described above. After electroporation 1 ml of SOC medium was added, incubated for 90 minutes, spread onto LB plates containing 25 μg/ml of chloramphenicol and incubated at 37° C. After 12 to 16 hours of growth at 37° C., colonies expressing the GFP protein could be easily visualized by illumination of plates with a hand held UV light.

As the gfpF0 primer binding site was deleted from the gfp gene cassette during deletion of the cl$^{ts857}$ gene, a new oligonucleotide primer, gfpEnt 5'-CCAGTTTGCTCAGGCTCT-3' (SEQ ID NO 19), was synthesized for PCR amplification the unrepressed gfp gene cassette. PCR amplification of the gfp cassette using gfpEnt and gfpR0 primers were performed using chloramphenicol resistant colonies obtained from electro-transformation with the unrepressed gfp cassette transposome. Correct sized PCR products indicated the presence of the unrepressed gfp gene cassette in all tested colonies. Four positive colonies from each of each *E. coli* and *Salmonella* strains were selected and grown overnight in liquid media (LB+chloramphenicol). Genomic DNA was then extracted from the cells using a DNA extraction kit (Fast DNA, BIO 101 systems). PCR product amplified from genomic DNA from two different transformants of each *E. coli* and *Salmonella* strain was used for nucleotide sequencing. All sequencing results confirmed the presence of the unrepressed gfp gene cassette in the genomic DNA of both *E. coli* and *Salmonella* transformants. These transformants were clearly fluorescent when grown on a range of agar plates and illuminated with a UV light.

Example 3

Identification of the Insertion Points of the Unrepressed gfp Gene Cassette into *E. coli* and *Salmonella* Integrant Chromosomes Genome walking PCR (GWPCR) was used for identification of the insertion points of the unrepressed gfp gene cassette into *E. coli* and *Salmonella* strains. Two genome walking primers were designed to walk upstream and downstream of the gfp gene cassette. Primer PENTGWF was used to genome walk from the 5' end of the gfp gene cassette and GFPGWR to walk from the 3' end of the cassette insertion point (See Table 1, FIGS. 2C and 2D).

Genomic walking PCRs and synthetic DNA linker assemblage were carried out according to the method described by Morris et al, Appl Environ Microbiol (1995) 61:2262-2269. The PENTGWF and GFPGWR primers were used in combination with primers complementary to the generic linker for GWPCR reactions. PCR products ranging from 300 bp to 800 bp were sequenced and results used for match searches in bacterial genomes database for identification of gfp gene cassette insertion points and flaking regions.

Insertion points of gfp gene cassette on the genomes of *E. coli* and *Salmonella* integrants were identified based on the published genome sequence data on *Salmonella typhimurium* and *E. coli* K12. For the fluorescent *E. coli* EC11775 strain, the gfp gene cassette was observed to be inserted into a gene encoding a homolog of *E. coli* K12 Zinc binding periplasmic protein (ZnaP). For the fluorescent *E. coli* BL21, the gfp gene cassette was inserted into a gene encoding 16S rRNA. For the fluorescent *Salmonella abaetetuba*, the gfp gene cassette was inserted into a gene homolog of *S. typhimurium* ATP-dependent helicase protein (hrpA). In the fluorescent *Salmonella typhimurium*, the gfp gene cassette was inserted into the sequence of a gene encoding a common antigen found in the outer membrane of *Salmonella* and other enterobacteria.

Example 4

Generation of Fluorescent *Listeria monocytogenes*

The strategy used to generate fluorescent *Listeria monocytogens* followed similar approach to that used for the *E. coli* and *Salmonella* strains. First, the gfp gene mut1 in an *E. coli/Listeria* shuttle vector pNF8 vector (Fortineau et al., 2000 Res Microbiol 151: 353-360) was replaced with our triple mutant gfp gene (gfp mut1 is a FACS optimized GFP with shifted excitation wavelength up to 488 nm). The gfp gene present in pEntPLGFP was amplified by PCR using the primers detailed in Table 3.

TABLE 3

| Name | Sequence | SEQ ID NO |
|---|---|---|
| Gfpmutf1 | 5'-AAACGGGATCCGAAAGGAGGTTTAT TAAAATGAGTAAAGGAGAAGAACTT | 24 |
| Gfpmutr1 | 5'-AAAAAACTGCAGTTATTTGTATAGTTCATCCATGCCA | 25 |

The gfpmut1F primer was designed to introduce a BamHI restriction enzyme site and a consensus gram-positive ribosome binding site and the reverse gfpmt1R primer was designed to introduce a PstI site in the PCR products. The resulting PCR product and the pNF8 were digested with BamHI and PstI restriction enzymes (MBI Fermentas), ligated using T4 ligase (Roche) and used to transform chemically competent *E. coli* DH5α cells. Recombinant cultures harbouring the newly generated plasmid vector were recovered from selective LB agar plates containing 150μ/mL of erythromycin (selective antibiotic resistance encoded in pNF8 vector). After incubation at 30° C. over 72 hr visibly green colonies appeared on plates (GFP expression in those recombinant clones in driven by the *Listeria* Pdlt promoter located just upstream of the gfp gene in the vector). Three putative recombinant clones were streaked onto fresh LB+erythromycin plates and single colonies used to inoculate LB+erythromycin liquid media followed by overnight incubation at 37° C. with shaking. In order to verify if the isolated pNF8 plasmid was carrying our triple mutant gfp gene and not the original FACS optimized GFP gfp gene mut1, an aliquot of the cultures were used for fluorescence assay measurements using a FLUOstar fluorimeter (BMG Lab Technologies GmbH). Two different excitation wavelengths—360 nm and 480 nm with fixed 520 nm emission were tested. Results showed high fluorescence from cells bearing the original pNF8 plasmid at 480 nm and lower fluorescence at 360 nm excitation, whereas opposite results for cells bearing the recombined triple mutant gfp with high fluorescence at 360 nm and lower fluorescence at 480 nm. One selected recombinant bearing the reconstructed vector named pNFMT1 was used for inoculation of LB liquid media containing 150 μl/mL erythromycin and incubated overnight at 37° C. The culture obtained was used for plasmid extraction using QIAprep kit (Qiagen).

*L. monocytogenes* electrocompetent cells were prepared by growing 250 ml of culture in brain and heart infusion (BHI) media containing 0.5 M of sucrose with shaking at 37° C. to optical density measured at 600 nm of 0.2. Penicillin was then added to 10 µl/ml and the culture grown to optical density measured at 600 nm of 0.5. Cells were cooled on ice and harvested by centrifugation at 4° C. and resuspended in 100 ml of ice cold 0.5 M sucrose in 1 mM HEPES pH 7.0 three times consecutively, then resuspended in 1 ml of ice cold 0.5 M sucrose in 1 mM HEPES pH 7.0, and stored as 50 µl aliquots at −80° C. Transformation efficiency of *L. monocytogenes* electrocompetent cells was evaluated using the pNFMT1 vector. Enumeration of fluorescent *L. monocytogenes* colonies LB agar plates containing 150µ/mL of erythromycin indicated transformation efficiencies up to $10^5$ c.f.u. per µg of pNFMT1 DNA.

The Pdlt promoter-mutant gfp gene construct present in the pNFMT1 was excised from the vector by restriction digest using EcoRI and Hind III restriction enzymes (MBI Fermentas). The pEntranceposon vector (Finnzymes) was also digested with EcoRI and Hind III restriction enzymes (MBI Fermentas). DNA corresponding to the digested Pdlt promoter-mutant gfp gene and the digested pEntranceposon vector were separated by agarose gel electrophoresis and purified from gels using a QIAquick gel extraction kit (Qiagen). The digested DNA was used for ligation using T4 ligase (Roche) for generation of the plasmid vector pEnt-Pdlt-GFPMT1. The pEnt-Pdlt-GFPMT1 vector was then used to transform competent *E. coli* DH5α cells. Recombinant cultures harbouring the vector pEnt-Pdlt-GFPMT1 were recovered from selective LB agar plates containing 25µ/ml of chloramphenicol (selective antibiotic resistance encoded in pEnt-Pdlt-GFPMT1 vector).

The pEnt-Pdlt-GFPMT1 vector was digested with BglII restriction enzyme and the excised CamR transposon fragment containing the Pdlt-gfp separated by agarose gel electrophoresis and purified using a QIAquick gel Extraction kit (Qiagen Inc). Purified CamR Pdlt-gfp transposon DNA was used for transpososome assembly reactions. Transpososome formation reactions were optimized by titration of the amount of CamR Pdlt-gfp gene transposon DNA against a fixed amount of MuA transposase enzyme (Finnzymes). Reagents for transpososome assembly reaction mixtures (20 µl) included ~6 pmol of MuA transposase, 50% glycerol, 150 mM of Tris-HCl (pH 6.0), 150 mM NaCl, 0.1 mM EDTA, and 0.025% (v/v) Triton X-100. Transpososome reactions were performed by adding ~0.25 pmol to ~1.0 pmol of Pdlt-gfp gene transposon DNA to the mixtures followed by incubating at 30° C. for 2-3 hours. Transpososome formation was visualized by electrophoresis on 2% agarose-TAE buffer gel containing 80 µg/ml of bovine serum albumen. Transpososome assembly reaction samples (1 µl) were loaded into the gel using 0.2 (v/v) of Ficoll 400 as loading buffer. After gel visualization, selected transpososome complexes were used for the transformation of *L. monocytogenes* electrocompetent cells. Aliquots of 1 µl of transpososome reactions were used for electroporation of 40 µl electrocompetent *L. monocytogenes* cells using a Genepulser (Bio-Rad) at the following settings: voltage 2.5 kV; capacitance 25 µF; resistance 200Ω (Bio-Rad 2-mm electrode spacing cuvettes). After electroporation 1 ml of BHI medium was added, incubated for 90 minutes, spread onto LB plates containing 25 µg/ml of chloramphenicol and incubated at 30° C.

Example 5

This section describes the expression of another fluorescent protein, a red fluorescent protein known as DsRed2, in *E. coli*. The Dsred2 was successfully integrated onto the chromosome of *E. coli* but no fluorescence was visible when examined under a UV light.

*E. coli* Containing Red Fluorescent Protein on a Plasmid

A gene cassette was constructed by placing T7 promoter and ribosomal binding site upstream of starting codon of DsRed2 gene (Clontech) using the primers T7promppf1 and Rfppr1 (see Table 1). The cassette, herein referred to as the T7DsRed2 gene cassette, was constructed then ligated into the pEntranceposon plasmid (Finnzymes). This plasmid was subsequently transformed into *E. coli* DH5 alpha cells.

Colonies of the plasmid containing *E. coli* showed a bright red fluorescence after two days of growth on agar containing chloramphenicol. Only weak fluorescence was observed after 24 hours growth.

Chromosomal Integration of Red Fluorescent Protein in *E. coli*

The pEntranceposon-CmR plasmid containing the T7-DsRed2 gene cassette was digested by BglII restriction enzyme digest and the released transposon used for MuA transpososome formation (Finnzymes). Aliquots of the transpososome formation were used for transformation of electrocompetent *E. coli* BL21(DE3) cells and chloramphenicol resistant transformants were recovered after incubation on plates for 18-24 hours at 37° C. Four transformants were isolated, chromosomal DNA extracted and analyzed for incorporation of T7DsRed2 gene into the chromosome by PCR. Results were positive for the clones tested, indicating the incorporation of T7DsRed2 gene into the genome of cultures. For one of the clones nucleotide sequencing was performed and the T7DsRed2 gene sequence was confirmed to be intact. Transformants were cultured under inducing conditions on media containing 1 mM IPTG, an inducer of transcription from the T7 promoter. However, no DSRed2 fluorescence could be detected from cultures when plates were illuminated with UV light.

Example 6

Stability of Fluorescent Strains

The fluorescence of the *E. coli, Listeria* and *Salmonella* integrant strains were examined to ensure that these organisms remained fluorescent when passaged multiple times.

Yeast extract broth was inoculated with each of the fluorescent *E. coli* and *Salmonella* strains. A broth of Brain Heart Infusion (Oxoid) was inoculated with the fluorescent *Listeria* strain. The cultures were incubated with shaking at 37° C. for 24 hours. A loopfull of culture was then streaked onto nutrient agar or in the case of *Listeria* onto blood agar and incubated at 37 C for 24 hours. The plates were then illuminated with a UV light and carefully examined for the presence of non-fluorescent colonies.

A colony from each plate was then used to inoculate another broth and the entire process was repeated. This continued for 10 rounds of culturing.

No non-fluorescent colonies were observed. An atypical fluorescent colony was observed with the *Salmonella abatetuba* culture. The colony appeared less smooth and flatter than the normal colonies for this strain. Biochemical analysis revealed that it was *Salmonella abatetuba* but a mutant that formed atypical colonies. It is likely that the repeated exposure to UV light caused the mutation. The mutant was still fluorescent.

These results demonstrate that the fluorescence gene is highly stable in these strains of bacteria.

SUMMARY

The present inventors have determined that three select modifications to the GFP protein, namely S72A, M153T and V163A, result is consistently higher visible expression of the protein when expressed in E. coli in a plasmid.

It has been determined that using the unrepressed lambda $P_L$ promoter, it is possible to constitutively express visibly detectable levels of the modified form of GFP from a single copy of the gfp gene integrated into the genome of 3 different strains of E. coli and two species of Salmonella. Initial experiments indicated that expression was stable through long periods of growth and cell division. Precise genomic integration points were determined for each of the E. coli and Salmonella gfp-cassette integrants.

Detectable levels of the modified GFP were observed when expressed in Listeria monocytogenes under the control of the Listeria Pdlt promoter.

Detectable levels of the modified GFP were not observed when expressed from a single copy integrated gene under the control of the lambda $ci^{ts857}$ repressor protein. Similarly, the fluorescent protein DsRed2 could not be detected when expressed from a single copy integrated gene under the control of a T7 RNA polymerase/T7 promoter system.

Means for the production of cells visibly altered by expression of a modified GFP protein have been developed that make them useful as QC strains in microbiological testing.

It should be appreciated that this technique is applicable to other bacterial species, and that other promoter systems and marker genes could be used in a similar fashion to achieve visible alteration of bacterial cells.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. An isolated modified bacterium forming a colony having fluorescence visible by the naked eye when the colony is illuminated by ultraviolet light, the modified bacterium comprising a mutated green fluorescent protein (GFP) gene from the jellyfish *Aequorea victoria* inserted into the chromosome of the modified bacterium; wherein the mutated GFP gene comprising a nucleic acid molecule consisting of mutations at nucleotide positions 1737 and 1739 of SEQ ID NO: 4 encoding Ser72Ala, nucleotide position 1981 of SEQ ID NO: 4 encoding Met153Thr and nucleotide position 2011of SEQ ID NO: 4 encoding Val163Ala, or the mutated GFP gene comprising a nucleic acid molecule consisting of mutations which encode amino acid changes Ser72Ala, Met153Thr, Val163 Ala of SEQ ID NO: 3, and wherein the mutated GFP gene is under the control of an un-repressed strong promoter.

2. The modified bacterium of claim 1 wherein the mutated GFP gene encodes a mutated GFP protein consisting of mutations Ser72Ala, Met153Thr, Val163 Ala of SEQ ID NO: 3.

3. The modified bacterium of claim 1 wherein the mutated GFP gene is inserted into the chromosome using a cassette comprising the mutant GFP gene under the control of the un-repressed strong promoter and one or more transposon elements.

4. The modified bacterium of claim 3 wherein the strong promoter is the bacteriophage lambda promoter left (PL).

5. The modified bacterium of claim 1 wherein the bacterium is selected from the group consisting of *Acinetobacter lwoffii, Aeromonas hydrophila, Aspergillus niger, Bacillus cereus, Bacillus subtilis, Campylobacter coli, Campylobacter jejuni, Candida albicans, Citrobacter freundii, Clostridium perfringens, Clostridium sporogenes, Edwardsiella tarda, Enterobacter aerogenes, Enterobacter cloacae, Enterococcus faecalis, Escherichia coli, Escherichia coli 0157, Haemophilus influenzae, Klebsiella pneumoniae, Klebsiella aerogenes, Lactobacillus acidophilus, Lactobacillus casei, Lactobacillus fermentus, Legionella pneumophila, Listeria innocua, Listeria ivanovii, Listeria monocytogenes, Staphylococcus aureus, Neisseria gonorrhoeae, Proteus rettgeri, Proteus mirabilis, Proteus vulgaris, Pseudomonas aeruginosa, Pseudomonas cepacia, Pseudomonas fluorescens, Rhodococcus equi, Salmonella abaetetuba, Saccharomyces cerevisiae, Salmonella salford, Salmonella menston, Salmonella sofia, Salmonella typhimurium, Salmonella poona, Serratia marcescens, Shigella sonnei, Staphylococcus aureus, Staphylococcus epidermidis, Streptococcus pneumoniae, Streptococcus pyogenes, Vibrio parahaemolyticus, Yersinia enterocolitica,* and *Zygosaccharomyces rouxii.*

6. The modified bacterium of claim 5 wherein the bacterium is *Escherichia coli, Salmonella salford, Salmonella menston, Salmonella sofia, Salmonella typhimurium, Salmonella poona, Listeria innocua, Listeria ivanovii,* or *Listeria monocytogenes.*

7. The modified bacterium of claim 6 wherein the bacterium is *Salmonella typhimurium, Salmonella abaetetuba,* or *Listeria monocytogenes.*

8. The modified bacterium of claim 1, wherein the modified bacterium is selected from the group consisting of National Measurement Institute (formerly Australian Government Analytical Laboratories) deposit accession numbers NM04/42817, NM04/42818, NM04/42819, and NM04/42820.

9. An isolated modified bacterium forming a colony having fluorescence visible by the naked eye when the colony is illuminated by ultraviolet light, the modified bacterium comprising a mutated green fluorescent protein (GPP) gene from the jellyfish *Aequorea victoria* inserted into the chromosome of the modified bacterium, the modified bacterium is selected from the group consisting of National Measurement Institute (formerly Australian Government Analytical Laboratories) deposit accession numbers NM04/42817, NM04/42818, NM04/42819, and NM04/42820.

10. The modified bacterium of claim 9 wherein the deposit accession number is NM04/42817.

11. The modified bacterium of claim 9 wherein the deposit accession number NM04/42818.

12. The modified bacterium of claim 9 wherein the deposit accession number NM04/42819.

13. The modified bacterium of claim 9 wherein the deposit accession number NM04/42820.

* * * * *

SEQUENCE LISTING

```
<160> NUMBER OF SEQ ID NOS: 25

<210> SEQ ID NO 1
<211> LENGTH: 2007
<212> TYPE: DNA
<213> ORGANISM: Artificial Sequence
<220> FEATURE:
<223> OTHER INFORMATION: gfp gene cassette

<400> SEQUENCE: 1
aaaaaaaaaa gtcgactcag ccaaacgtct cttcaggcca ctgactagcg ataactttcc      60
ccacaacgga acaactctca ttgcatggga tcattgggta ctgtgggttt agtggttgta     120
aaaacacctg accgctatcc ctgatcagtt tcttgaaggt aaactcatca cccccaagtc     180
tggctatgca gaaatcacct ggctcaacag cctgctcagg gtcaacgaga attaacattc     240
cgtcaggaaa gcttggcttg gagcctgttg gtgcggtcat ggaattacct tcaacctcaa     300
gccagaatgc agaatcactg gcttttttgg ttgtgcttac ccatctctcc gcatcacctt     360
tggtaaaggt tctaagctta ggtgagaaca tccctgcctg aacatgagaa aaaacagggt     420
actcatactc acttctaagt gacggctgca tactaaccgc ttcatacatc tcgtagattt     480
ctctggcgat tgaagggcta aattcttcaa cgctaacttt gagaattttt gtaagcaatg     540
cggcgttata agcatttaat gcattgatgc cattaaataa agcaccaacg cctgactgcc     600
ccatccccat cttgtctgcg acagattcct gggataagcc aagttcattt ttcttttttt     660
cataaattgc tttaaggcga cgtgcgtcct caagctgctc ttgtgttaat ggtttctttt     720
ttgtgctcat acgttaaatc tatcaccgca agggataaat atctaacacc gtgcgtgttg     780
actattttac ctctggcggt gataatggtt gcatgtacta aggaggttgt atggaacaac     840
gcataaccct gaaagattat gcaatgcgct ttgggcaaac caagacagct aaagatcaag     900
aatgttgatc ttcagtgttt cgcctgtctg ttttgcaccg gaatttttga gttctgccgt     960
ttatcgcccg gggatctctc acctaccaaa caatgccccc ctgcaaaaaa taaattcata    1020
taaaaaacat acagataacc atctgcggtg ataaattatc tctggcggtg ttgacataaa    1080
taccactggc ggtgatactg agcacatcag caggacgcac tgaccaccat gaaggtgacg    1140
ctcttaaaaa ttaagccctg aagaagggca gcattcaaag cagaaggctt tggggtgtgt    1200
gatacgaaac gaagcattgg cgcctcgagt aatttaccaa cactactacg ttttaactga    1260
aacaaactgg agactgccat gagtaaagga gaagaacttt tcactggagt tgtcccaatt    1320
cttgttgaat tagatggtga tgttaatggg cacaaatttt ctgtcagtgg agagggtgaa    1380
```

-continued

```
ggtgatgcaa catacggaaa acttaccctt aaatttattt gcactactgg aaaactacct    1440
gttccatggc caacacttgt cactactttc ksktatggts ttcaatgctt tkcragatac    1500
ccagatcata tgaaacggca tgacttttc aagagtgcca tgcccgaagg ttatgtacag     1560
gaaagaacta tatytttcaa agatgacggg aactacaaga cacgtgctga agtcaagttt    1620
gaaggtgata cccttgttaa tagaatcgag ttaaaaggta ttgattttaa agaagatgga    1680
aacattcttg gacacaaatt ggaatacaac tataactcac acaatgtata catcatygca    1740
gacaaacaaa agaatggaat caaagytaac ttcaaaatta gacacaacat tgaagatgga    1800
agcgttcaac tagcagacca ttatcaacaa aatactccaa ttggcgatgg ccctgtcctt    1860
ttaccagaca accattacct gtccacacaa tctgcccttt cgaaagatcc caacgaaaag    1920
agagaccaca tggtccttct tgagtttgta acagctgctg ggattacaca tggcatggat    1980
gaactataca aataagaatt caaaaaa                                        2007
```

<210> SEQ ID NO 2
<211> LENGTH: 237
<212> TYPE: PRT
<213> ORGANISM: Unknown
<220> FEATURE:
<223> OTHER INFORMATION: phage lambda clts857

<400> SEQUENCE: 2

```
Gly Phe Thr Glu Glu Pro Trp Gln Ser Ala Ile Val Lys Gly Val Val
1               5                   10                  15

Ser Cys Ser Glu Asn Cys Pro Ile Met Pro Tyr Gln Pro Asn Leu Pro
            20                  25                  30

Gln Leu Phe Val Gln Gly Ser Asp Arg Ile Leu Lys Lys Phe Thr Phe
        35                  40                  45

Glu Asp Gly Gly Leu Arg Ala Ile Cys Phe Asp Gly Pro Glu Val Ala
    50                  55                  60

Gln Glu Pro Asp Val Leu Ile Leu Met Gly Asp Pro Phe Ser Pro Lys
65                  70                  75                  80

Ser Gly Thr Pro Ala Thr Met Ser Asn Gly Glu Val Glu Leu Trp Phe
                85                  90                  95

Ala Ser Asp Ser Ala Lys Lys Thr Thr Ser Val Trp Arg Glu Ala Asp
            100                 105                 110

Gly Lys Thr Phe Thr Arg Leu Lys Pro Ser Phe Met Gly Ala Gln Val
        115                 120                 125

His Ser Phe Val Pro Tyr Glu Tyr Glu Ser Arg Leu Ser Pro Gln Met
    130                 135                 140

Ser Val Ala Glu Tyr Met Glu Tyr Ile Glu Arg Ala Ile Ser Pro Ser
145                 150                 155                 160

Phe Glu Glu Val Ser Val Lys Leu Ile Lys Thr Leu Ala Ala Asn
                165                 170                 175

Tyr Ala Asn Leu Ala Asn Ile Gly Asn Phe Leu Ala Gly Val Gly Ser
            180                 185                 190

Gln Gly Met Gly Met Lys Asp Ala Val Ser Glu Gln Ser Leu Gly Leu
        195                 200                 205

Glu Asn Lys Lys Lys Glu Tyr Ile Ala Lys Leu Arg Arg Ala Asp Glu
    210                 215                 220

Leu Gln Glu Gln Thr Leu Pro Lys Lys Thr Ser Met
225                 230                 235
```

<210> SEQ ID NO 3
<211> LENGTH: 238
<212> TYPE: PRT
<213> ORGANISM: Aequorea victoria

<400> SEQUENCE: 3

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
50                  55                  60

Ser Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
210                 215                 220

Thr Ala Ala Gly Ile Thr His Gly Met Asp Glu Leu Tyr Lys
225                 230                 235

<210> SEQ ID NO 4
<211> LENGTH: 2326
<212> TYPE: DNA
<213> ORGANISM: Artificial Sequence
<220> FEATURE:
<223> OTHER INFORMATION: gfp gene cassette

<400> SEQUENCE: 4
agatctgaag cggcgcacga aaacgcgaaa agcgtttcac gataaatgcg aaaacggatc    60
cttttcgacc gaataaatac ctgtgacgga agatcacttc gcagaataaa taatcctggg   120
tgtccctgtt gataccggga agccctgggc caacttttgg cgaaaatgag acgttgatcg   180
gcacgtaaga ggttccaact ttcaccataa tgaaataaga tcactaccgg gcgtattttt   240
tgagttgtcg agattttcag gagctaagga agctaaaatg gagaaaaaaa tcactggata   300
taccaccgtt gatatatccc aatggcatcg taaagaacat tttgaggcat ttcagtcagt   360
tgctcaatgt acctataacc agaccgttca gctggatatt acggcctttt taaagaccgt   420
aaagaaaaat aagcacaagt tttatccggc ctttattcac attcttgccc gcctgatgaa   480
tgctcatccg gaattacgta tggcaatgaa agacggtgag ctggtgatat gggatagtgt   540

-continued

```
tcacccttgt tacaccgttt tccatgagca aactgaaacg ttttcatcgc tctggagtga      600
ataccacgac gatttccggc agtttctaca catatattcg caagatgtgg cgtgttacgg      660
tgaaaacctg gcctatttcc ctaaagggtt tattgagaat atgttttcg tctcagccaa       720 tccctgggtg agtttcacca gttttgattt aaacgtggcc aatatggaca acttcttcgc      780
ccccgttttc accatgggca atattatac gcaaggcgac aaggtgctga tgccgctggc       840
gattcaggtt catcatgccg tttgtgatgg cttccatgtc ggcagaatgc ttaatgaatt      900
acaacagtac tgcgatgagt ggcagggcgg ggcgtaattt ttttaaggca gttattggtg      960 ccccttaaacg cctggttgct acgcctgaat aagtgataat aagcggatga atggcagaaa   1020
ttcgaaagca aattcgaccc ggtcgtcggt tcagggcagg gtcgttaaat agccgcttat     1080
gtctattgct ggtttaccgg tttattgact accggaagca gtgtgaccgt gtgcttctca     1140
aatgcctgag gccagtttgc tcaggctctc cccgtggagg taataattga cgataggatc     1200
cgcggccggc cgatggggat ctctcaccta ccaaacaatg ccccctgca aaaataaat       1260 tcatataaaa aacatacaga taaccatctg cggtgataaa ttatctctgg cggtgttgac     1320
ataaatacca ctggcggtga tactgagcac atcagcagga cgcactgacc accatgaagg     1380
tgacgctctt aaaaattaag ccctgaagaa gggcagcatt caaagcagaa ggctttgggg     1440
tgtgtgatac gaaacgaagc attggcgcct cgagtaattt accaacacta ctacgtttta     1500
actgaaacaa actggagact gccatgagta aaggagaaga acttttcact ggagttgtcc     1560
caattcttgt tgaattagat ggtgatgtta atgggcacaa attttctgtc agtggagagg     1620
gtgaaggtga tgcaacatac ggaaaactta cccttaaatt tatttgcact actggaaaac    1680
tacctgttcc atggccaaca cttgtcacta ctttctctta tggtgttcaa tgctttgcga    1740
gatacccaga tcatatgaaa cggcatgact ttttcaagag tgccatgccc gaaggttatg    1800
tacaggaaag aactatattt ttcaaagatg acgggaacta caagacacgt gctgaagtca    1860
agtttgaagg tgatacccctt gttaatagaa tcgagttaaa aggtattgat tttaaagaag    1920
atggaaacat tcttggacac aaattggaat acaactataa ctcacacaat gtatacatca    1980
cggcagacaa acaaaagaat ggaatcaaag ctaacttcaa aattagacac aacattgaag    2040
atggaagcgt tcaactagca gaccattatc aacaaaatac tccaattggc gatggccctg    2100
tccttttacc agacaaccat tacctgtcca cacaatctgc cctttcgaaa gatcccaacg    2160
aaaagagaga ccacatggtc cttcttgagt ttgtaacagc tgctgggatt acacatggca    2220
tggatgaact atacaaataa gaattctcta gatgatcagc ggccgcgatc cgttttcgca    2280
tttatcgtga aacgctttcg cgtttttcgt gcgccgcttc agatct                    2326
```

<210> SEQ ID NO 5
<211> LENGTH: 219
<212> TYPE: PRT
<213> ORGANISM: Unknown
<220> FEATURE:
<223> OTHER INFORMATION: chloramphenicol resistance gene

<400> SEQUENCE: 5

```
Met Glu Lys Lys Ile Thr Gly Tyr Thr Thr Val Asp Ile Ser Gln Trp
1               5                   10                  15

His Arg Lys Glu His Phe Glu Ala Phe Gln Ser Val Ala Gln Cys Thr
            20                  25                  30

Tyr Asn Gln Thr Val Gln Leu Asp Ile Thr Ala Phe Leu Lys Thr Val
        35                  40                  45
```

```
Lys Lys Asn Lys His Lys Phe Tyr Pro Ala Phe Ile His Ile Leu Ala
     50                  55                  60

Arg Leu Met Asn Ala His Pro Glu Leu Arg Met Ala Met Lys Asp Gly
 65                  70                  75                  80

Glu Leu Val Ile Trp Asp Ser Val His Pro Cys Tyr Thr Val Phe His
                 85                  90                  95

Glu Gln Thr Glu Thr Phe Ser Ser Leu Trp Ser Glu Tyr His Asp Asp
            100                 105                 110

Phe Arg Gln Phe Leu His Ile Tyr Ser Gln Asp Val Ala Cys Tyr Gly
        115                 120                 125

Glu Asn Leu Ala Tyr Phe Pro Lys Gly Phe Ile Glu Asn Met Phe Phe
    130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val His
            180                 185                 190

His Ala Val Cys Asp Gly Phe His Val Gly Arg Met Leu Asn Glu Leu
        195                 200                 205

Gln Gln Tyr Cys Asp Glu Trp Gln Gly Gly Ala
    210                 215

<210> SEQ ID NO 6
<211> LENGTH: 238
<212> TYPE: PRT
<213> ORGANISM: Aequorea victoria

<400> SEQUENCE: 6

Met Ser Lys Gly Glu Glu Leu Phe Thr Gly Val Val Pro Ile Leu Val
 1               5                  10                  15

Glu Leu Asp Gly Asp Val Asn Gly His Lys Phe Ser Val Ser Gly Glu
             20                  25                  30

Gly Glu Gly Asp Ala Thr Tyr Gly Lys Leu Thr Leu Lys Phe Ile Cys
         35                  40                  45

Thr Thr Gly Lys Leu Pro Val Pro Trp Pro Thr Leu Val Thr Thr Phe
 50                  55                  60

Ser Tyr Gly Val Gln Cys Phe Ala Arg Tyr Pro Asp His Met Lys Arg
 65                  70                  75                  80

His Asp Phe Phe Lys Ser Ala Met Pro Glu Gly Tyr Val Gln Glu Arg
                 85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
```

```
            195                 200                 205
Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 7
<211> LENGTH: 1032
<212> TYPE: DNA
<213> ORGANISM: Artificial Sequence
<220> FEATURE:
<223> OTHER INFORMATION: gfp gene cassette

<400> SEQUENCE: 7
ggggatctct cacctaccaa acaatgcccc cctgcaaaaa ataaattcat ataaaaaaca      60
tacagataac catctgcggt gataaattat ctctggcggt gttgacataa ataccactgg     120
cggtgatact gagcacatca gcaggacgca ctgaccacca tgaaggtgac gctcttaaaa     180
attaagccct gaagaagggc agcattcaaa gcagaaggct ttggggtgtg tgatacgaaa     240
cgaagcattg gcgcctcgag taatttacca acactactac gttttaactg aaacaaactg     300
gagactgcca tgagtaaagg agaagaactt ttcactggag ttgtcccaat tcttgttgaa     360
ttagatggtg atgttaatgg gcacaaattt tctgtcagtg agagggtga aggtgatgca      420 acatacggaa aacttaccct taaatttatt tgcactactg gaaaactacc tgttccatgg     480
ccaacacttg tcactacttt ctcttatggt gttcaatgct ttgcgagata cccagatcat     540
atgaaacggc atgacttttt caagagtgcc atgcccgaag ttatgtaca ggaaagaact      600 atattttca aagatgacgg gaactacaag acacgtgctg aagtcaagtt tgaaggtgat     660
acccttgtta atagaatcga gttaaaaggt attgatttta agaagatgg aaacattctt     720 ggacacaaat tggaatacaa ctataactca cacaatgtat acatcacggc agacaaacaa     780
aagaatggaa tcaaagctaa cttcaaaatt agacacaaca ttgaagatgg aagcgttcaa     840
ctagcagacc attatcaaca aaatactcca attggcgatg gccctgtcct tttaccagac     900
aaccattacc tgtccacaca atctgcccct tcgaaagatc ccaacgaaaa gagagaccac     960
atggtccttc ttgagtttgt aacagctgct gggattacac atggcatgga tgaactatac    1020
aaataagaat tc                                                        1032

<210> SEQ ID NO 8
<211> LENGTH: 238
<212> TYPE: PRT
<213> ORGANISM: Aequorea victoria

<400> SEQUENCE: 8

Met Ser Lys Gly Glu Glu Leu Phe Thr Gly Val Pro Ile Leu Val
1               5                   10                  15

Glu Leu Asp Gly Asp Val Asn Gly His Lys Phe Ser Val Ser Gly Glu
                20                  25                  30

Gly Glu Gly Asp Ala Thr Tyr Gly Lys Leu Thr Leu Lys Phe Ile Cys
            35                  40                  45

Thr Thr Gly Lys Leu Pro Val Pro Trp Pro Thr Leu Val Thr Thr Phe
        50                  55                  60

Ser Tyr Gly Val Gln Cys Phe Ala Arg Tyr Pro Asp His Met Lys Arg
65                  70                  75                  80

His Asp Phe Phe Lys Ser Ala Met Pro Glu Gly Tyr Val Gln Glu Arg
                85                  90                  95
```

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 9
<211> LENGTH: 30
<212> TYPE: DNA
<213> ORGANISM: Artificial Sequence
<220> FEATURE:
<223> OTHER INFORMATION: degenerate oligonucleotide primer for modified
      gfp gene construction

<400> SEQUENCE: 9 tttttgaat tcttatttgt atagttcatc                                         30

<210> SEQ ID NO 10
<211> LENGTH: 27
<212> TYPE: DNA
<213> ORGANISM: Artificial Sequence
<220> FEATURE:
<223> OTHER INFORMATION: degenerate oligonucleotide primer for modified
      gfp gene construction

<400> SEQUENCE: 10
ctttactcat ggcagtctcc agtttgt                                           27

<210> SEQ ID NO 11
<211> LENGTH: 26
<212> TYPE: DNA
<213> ORGANISM: Artificial Sequence
<220> FEATURE:
<223> OTHER INFORMATION: degenerate oligonucleotide primer for modified
      gfp gene construction

<400> SEQUENCE: 11
gagactgcca tgagtaaagg agaaga                                            26

<210> SEQ ID NO 12
<211> LENGTH: 36
<212> TYPE: DNA
<213> ORGANISM: Artificial Sequence
<220> FEATURE:
<223> OTHER INFORMATION: degenerate oligonucleotide primer for modified
      gfp gene construction

<400> SEQUENCE: 12
atggtsttca atgctttkcr agatacccag atcata                                 36

<210> SEQ ID NO 13
<211> LENGTH: 26
<212> TYPE: DNA
<213> ORGANISM: Artificial Sequence
<220> FEATURE:
<223> OTHER INFORMATION: degenerate oligonucleotide primer for modified
      gfp gene construction

<400> SEQUENCE: 13
aactatatyt ttcaaagatg acggga                                          26

<210> SEQ ID NO 14
<211> LENGTH: 40
<212> TYPE: DNA
<213> ORGANISM: Artificial Sequence
<220> FEATURE:
<223> OTHER INFORMATION: degenerate oligonucleotide primer for modified
      gfp gene construction

<400> SEQUENCE: 14
caaacaaaag aatggaatca aagytaactt caaaattaga                            40

<210> SEQ ID NO 15
<211> LENGTH: 30
<212> TYPE: DNA
<213> ORGANISM: Artificial Sequence
<220> FEATURE:
<223> OTHER INFORMATION: degenerate oligonucleotide primer for modified
      gfp gene construction

<400> SEQUENCE: 15 tttttttgaat tcttatttgt atagttcatc                                     30

<210> SEQ ID NO 16
<211> LENGTH: 37
<212> TYPE: DNA
<213> ORGANISM: Artificial Sequence
<220> FEATURE:
<223> OTHER INFORMATION: degenerate oligonucleotide primer for modified
      gfp gene construction

<400> SEQUENCE: 16
aaagcattga asaccatams mgaaagtagt gacaagt                              37

<210> SEQ ID NO 17
<211> LENGTH: 27
<212> TYPE: DNA
<213> ORGANISM: Artificial Sequence
<220> FEATURE:
<223> OTHER INFORMATION: degenerate oligonucleotide primer for modified
      gfp gene construction

<400> SEQUENCE: 17
ctttgaaara tatagttctt tcctgta                                         27

<210> SEQ ID NO 18
<211> LENGTH: 41
<212> TYPE: DNA
<213> ORGANISM: Artificial Sequence
<220> FEATURE:
<223> OTHER INFORMATION: degenerate oligonucleotide primer for modified
      gfp gene construction

<400> SEQUENCE: 18
ttccattctt tgtttgtct gccrtgatgt atacattgtg t                          41

```
<210> SEQ ID NO 19
<211> LENGTH: 18
<212> TYPE: DNA
<213> ORGANISM: Artificial Sequence
<220> FEATURE:
<223> OTHER INFORMATION: degenerate oligonucleotide primer for modified
      gfp gene construction

<400> SEQUENCE: 19
ccagtttgct caggctct                                                    18

<210> SEQ ID NO 20
<211> LENGTH: 64
<212> TYPE: DNA
<213> ORGANISM: Artificial Sequence
<220> FEATURE:
<223> OTHER INFORMATION: degenerate oligonucleotide primer for modified
      gfp gene construction

<400> SEQUENCE: 20
ggggaattct taatacgact cactataga a ggagatatac atatggcctc cgagaacgtc     60
atca                                                                  64

<210> SEQ ID NO 21
<211> LENGTH: 31
<212> TYPE: DNA
<213> ORGANISM: Artificial Sequence
<220> FEATURE:
<223> OTHER INFORMATION: degenerate oligonucleotide primer for modified
      gfp gene construction

<400> SEQUENCE: 21
gggggggtcg acctacagga acaggtggtg g                                    31

<210> SEQ ID NO 22
<211> LENGTH: 18
<212> TYPE: DNA
<213> ORGANISM: Artificial Sequence
<220> FEATURE:
<223> OTHER INFORMATION: degenerate oligonucleotide primer for modified
      gfp gene construction

<400> SEQUENCE: 22
tgatcttccg tcacaggt                                                    18

<210> SEQ ID NO 23
<211> LENGTH: 18
<212> TYPE: DNA
<213> ORGANISM: Artificial Sequence
<220> FEATURE:
<223> OTHER INFORMATION: degenerate oligonucleotide primer for modified
      gfp gene construction

<400> SEQUENCE: 23
gtaacagctg ctgggatt                                                    18

<210> SEQ ID NO 24
<211> LENGTH: 50
<212> TYPE: DNA
<213> ORGANISM: Artificial Sequence
<220> FEATURE:
<223> OTHER INFORMATION: PCR primer for pEntPLGFP

<400> SEQUENCE: 24
aaacgggatc cgaaaggagg tttattaaaa tgagtaaagg agaagaactt                 50
```

```
<210> SEQ ID NO 25
<211> LENGTH: 37
<212> TYPE: DNA
<213> ORGANISM: Artificial Sequence
<220> FEATURE:
<223> OTHER INFORMATION: PCR primer for pEntPLGFP

<400> SEQUENCE: 25
aaaaaactgc agttatttgt atagttcatc catgcca                              37
```